US006981422B1

(12) United States Patent
Comardo

(10) Patent No.: US 6,981,422 B1
(45) Date of Patent: Jan. 3, 2006

(54) METHOD AND APPARATUS FOR DIFFERENTIAL PRESSURE TESTING OF CATALYTIC REACTOR TUBES

(76) Inventor: Mathis P. Comardo, 7042 Satsuma Dr., Houston, TX (US) 77041

( * ) Notice: Subject to any disclaimer, the term of this patent is extended or adjusted under 35 U.S.C. 154(b) by 0 days.

(21) Appl. No.: 10/965,338

(22) Filed: Oct. 14, 2004

(51) Int. Cl.
*G01L 7/00* (2006.01)
(52) U.S. Cl. ...................................................... 73/756
(58) Field of Classification Search ................ 208/110, 208/112, 250; 73/700, 714, 756
See application file for complete search history.

(56) References Cited

U.S. PATENT DOCUMENTS

| | | | |
|---|---|---|---|
| 4,128,473 A * | 12/1978 | Karr et al. ................... | 208/108 |
| 4,701,101 A | 10/1987 | Sapoff | |
| 5,890,868 A | 4/1999 | Comardo | |
| 5,897,282 A | 4/1999 | Comardo | |
| 6,725,706 B2 | 4/2004 | Johns et al. | |

OTHER PUBLICATIONS

Gulf Catalyst—DP-Tester—May 14, 1999 (Author unknown).

* cited by examiner

Primary Examiner—William Oen
(74) Attorney, Agent, or Firm—James L. Jackson

(57) ABSTRACT

A multi-tube differential pressure (Delta P) testing system for testing catalyst filled tubes of tube and shell type catalytic reactors has at least one mobile test unit for movement on the upper tube sheet of a catalytic reactor. An array of test probes is mounted to the mobile test unit and is selectively positionable in sealed gas pressure communicating engagement within the upper ends of selected reactor tubes. A pressure testing gas delivery system is interconnected with the test probes and selectively communicates pressurized gas to the testing tubes at a blow-down pressure or selected test pressure determined by restricted orifices. A differential pressure measurement system measures the back-pressure resulting from application of test pressure to individual reactor tubes and having a computer receiving electronic back-pressure measurement data and producing an electronic and/or visual record correlated with a reactor tube numerical sequence and identifying the resulting back-pressure of each reactor tube of the multi-tube test. The testing system is capable of selectively electronically counting in normal sequence and in inverted sequence to accommodate test unit orientation and incorporates a separate manually positioned testing wand to accommodate tube positions of the reactor that cannot be readily accessed by one or more of the array of test probes.

48 Claims, 11 Drawing Sheets

METHOD AND APPARATUS FOR DIFFERENTIAL PRESSURE TESTING OF CATALYTIC REACTOR TUBES

RELATED PATENT

The subject matter hereof relates to U.S. Pat. No. 6,694,902 of Mathis P. Comardo, entitled "Delta P Testing System for Tube and Shell Type Catalytic Reactors", issued on Feb. 24, 2004.

BACKGROUND OF THE INVENTION

1. Field of the Invention

The present invention relates generally to tube and shell type catalytic reactors having a large number of catalyst containing tubes which are supported in a reactor chamber by upper and lower tube support sheets and which contain catalyst pellets for accomplishing a catalytic reaction with a fluid flowing through the catalyst containing tubes. More particularly, the present invention concerns a testing system for measuring differential pressure of the catalyst containing reaction tubes by introducing pressure at a predetermined flow rate into selected tubes and by reading the back-pressure of the tubes through a transmitter. Even more particularly, the present invention concerns methods and apparatus for identifying and recording back-pressure test data of each of the numerous reactor tubes of catalytic reactors both electronically and by computer print-out. The present invention also concerns apparatus enabling back-pressure testing activity for catalyst tubes that are difficult to access due to their location within the reactor and for accommodating and recording the presence of disabled reactor tube positions that exist due to plugging of faulty reactor tubes or when tube positions are used for thermocouples or other sensing devices.

2. Description of the Prior Art

Tube and shell type catalytic reactors are typically of cylindrical configuration, having a cylindrical outer pressure containing wall for containing reaction fluids. Upper and lower tube sheets are typically welded to the upper and lower ends of the outer cylindrical wall or shell, so as to be oriented in parallel relation with one another. Intermediate tube sheets, between the upper and lower tube sheets, may also be mounted to the outer shell in the same manner. The reactor tubes are typically welded to the upper and lower tube sheets at a multiplicity of holes in the tube sheets, so that process fluids may flow from above or below the tube sheets through the passages of the reactor tubes and thus through the catalyst pellets that fill or partially fill the reactor tubes, causing the catalyst to react with the process fluid to provide the desired reaction and yield a desired fluid product. Tube and shell type catalytic reactors also have upper and lower domed closures that are typically removably secured to the cylindrical outer shell by means of a multiplicity of bolts or threaded studs. The upper and lower domed closures are removable to permit the reactor to be serviced, repaired or overhauled. Some catalytic reactors provide man-way openings in the domed closures, thus permitting the reactors to be serviced without removal of the closures. In this case, the reactor closures are of sufficient internal height above the upper tube sheet that a service worker, having removed a man-way closure and entered the reactor via the man-way, is able to stand on the upper tube sheet and accomplish reactor tube cleaning, catalyst replacement and DP testing activities.

From time to time the catalyst pellets within the reactor tubes will become substantially spent and the quality of the reaction thereof with the process fluid will become degraded. By conducting periodic tests of the reacted product being yielded by reaction with the catalyst of the reactor tubes, a determination can be made to shut down the reactor and overhaul the reactor by removing the spent catalyst from the reactor tubes and replacing the spent catalyst with new catalyst material. After the reactor tubes have been filled with one or more catalyst materials, typically in pellet form, a small quantity of dust is typically present in the reactor tubes along with the catalyst pellets. This dust may interfere with the flow of process fluid through the reactor tubes. Thus it is often desirable to subject the reactor tubes to "blow-down" prior to remove any residual dust prior to subjecting the filled reactor tubes to testing. Reactor tube blow-down is typically accomplished by injecting a high volume of air into the upper ends of the reactor tubes to entrain the dust within the flowing air so that the dust and air exit the lower ends of the reactor tubes below the lower tube sheet of the reactor. The displaced dust is captured and retained by a dust collector and is disposed of in a manner that is safe for personnel and the environment. Reactor tube blow-down is typically done in association with differential pressure testing of the reactor tubes.

To determine the quality of a catalyst loading procedure and to ensure the efficiency of a catalytic reactor process, prior to placing the reactor back in service, some and preferably all of the filled or loaded reactor tubes are tested. The condition of the catalyst loading of the reactor tubes can be detected by measurement of the back pressure of gas, typically air, being forced through the reactor tubes at a predetermined pressure and rate of flow. This test, known as a differential pressure or Delta P or D-P test, will also permit any leaking or otherwise faulty reactor tubes to be detected, so that they can be taken out of service, such as by welding plugs into the upper and lower tube openings. Also, since as mentioned above some of the tube openings may be closed at the upper tube sheet by thermocouples and other temperature, pressure or process sensing devices that have been installed, these non-serviceable reactor tubes are identified as a non-serviceable tube position in the resulting reactor service report. To enable loading of the reactor tubes with catalyst and to conduct D-P tests for filled reactor tubes, personnel will gain access to the upper tube sheet via a man-way in an upper reactor shell member or by removing the upper reactor shell member.

Differential pressure testing of reactor tubes is typically considered necessary or desirable after spent catalyst has been replaced with new catalyst material. If the tubes have been properly filled with catalyst material, each of the multiplicity of reactor tubes will have substantially the same back-pressure when differential pressure testing is accomplished. If any of the reactor tubes are improperly filled, as indicated by excessively high or unusually low back-pressure measurement the catalyst material thereof can be removed and the tube can be refilled. If not properly filled, certain catalyst tubes of the reactor can develop hot spots within the reactor which may cause the process quality of the reactor to degrade earlier than expected or it can cause an improper process reaction to occur, so that the quality of the resulting product can be less than optimum.

In the past, D-P testing of reactor tubes has been done by using a testing device that is capable of testing a single tube and by achieving a differential pressure test that can be visually inspected by the worker conducting the test, but providing no electronic or printed test report for each reactor tube that has been tested. Since present day catalytic reactors may have from 20,000 to 40,000 or even 80,000 reactor tubes it is impractical to test each reactor tube due to the significant labor costs and the length of reactor down time that would be required. Accordingly, it is desirable to provide a mechanism for simultaneously conducting differential pressure testing of a plurality of reactor tubes, for example 8 to 10 tubes or more, to facilitate rapid and simplified reactor tube testing so that all of the reactor tubes of a tube and shell type catalytic reactor can be quickly and efficiently tested in a manner requiring a minimum of labor and a minimum level of technical skill of the worker conducting the test. It is also desirable to provide the test results of differential pressure reactor tube testing in the form of an electronically documented read-out that can be presented in the form of a computer screed display and/or a paper or hard copy, permitting the state of each of the reactor tubes to be individually indicated and a permanent record of the DP test results of each of the multiplicity of reactor tubes to be established and recorded. Further, it is desirable to provide a rather complex reactor tube differential pressure testing system and testing procedure that is simple and efficient for rapid use by relatively unskilled workers and which yields quality test results with minimum time and costs for achieving testing of each of the filled reactor tubes of a reactor. It is also desirable to ensure that testing of each of the multiplicity of reactor tubes is accomplished and that inactive reactor tube positions due to plugged faulty tubes and tube positions having thermocouples or other sensing devices are also specifically identified and recorded as such. It is also desirable to permit filled reactor tube blow-down to be accomplished through the use of the multitube differential pressure testing system and yet enable a higher volume of air to be injected into the reactor tubes to accomplish efficient removal of dust and other debris during blow-down as compared with the volume of air used for differential pressure testing.

2. Description of the Prior Arts

Various apparatus for differential pressure testing of the filled reactor tubes of tube and shell type catalytic reactors has been developed and utilized. Early on, manual reactor tube testing apparatus was developed and utilized that permits manual selection and differential pressure testing to be accomplished, one tube at a time. Thus, with many tube and shell type catalytic reactors having as many as 20,000 reactor tubes and some reactors having from 40,000 to 80,000 reactor tubes, this manual testing apparatus is typically utilized by randomly selecting and testing some of the reactor tubes after all of the tubes have been filled with catalyst material. This single tube testing apparatus presents some test data in the form of a visual back pressure indication, but does not provide any sort of electronic read-out or computer print-out that can be inspected and maintained as a record. This single tube testing apparatus is typically composed of interconnected pipe sections having a lower resilient seal element for sealing its lower end with a selected reactor tube opening. The lower section of the apparatus functions as an air supply through which air is injected into the selected reactor tube. A pressure regulator is mounted to the piping to regulate air pressure being delivered to the unit via a supply hose that is connected to the piping by a quick-disconnect fitting, with the air supply being controlled by a simple on-off valve. A pressure gauge is provided in the piping to visually indicate the air pressure being supplied and a differential pressure monitor is also mounted to the unit for visual inspection of measured back-pressure by the person using the apparatus and being coupled by a tube to the piping at a point below an orifice element. To enable the tapered lower resilient seal element of the unit to establish sealing engagement with a selected reactor tube opening of the upper tube sheet, a lateral pipe section is provided which is engaged by the foot of the user to permit sufficient downward manual force to be applied to deform the tapered lower resilient element against the upper end of the selected reactor tube within a reactor tube opening to effect sealing thereof with the upper end of a reactor tube. With the reactor tube seal being maintained by this foot actuated force, the user will then actuate a valve control lever moving the valve to its open condition to admit regulated gas pressure into the reactor tube. The worker will then read the test data indicia that is present on the back-pressure gauge. Typically, no record of the test data is kept. The user merely arrives at a conclusion, based on random back-pressure tests, concerning the overall accuracy of the tube cleaning and replacement catalyst loading procedure. If the back-pressure of a reactor tube clearly indicates improper reactor tube loading, the user will often make a mark on the upper tube sheet or place a colored marker on a reactor tube opening indicating that the improperly loaded reactor tube must be emptied of catalyst pellets and again filled and tested. Using this method of testing, it is clear that a number of improperly filled catalyst tubes may not be tested and thus the overall integrity of the reactor servicing operation may be less than optimal.

More recently, multi-tube blow-down and D-P testing devices have been developed as indicated by U.S. Pat. No. 6,694,802 of Comardo, which covers a predecessor to the present invention and is identified above as a related patent, and U.S. Pat. No. 6,725,706 of Johns, et al. These multi-tube D-P testing devices have provided reactor owners and service personnel with the capability of mechanized testing of reactor tubes and the capability of achieving test reports in the form of electronic data or hard copies that identify the test parameters of individual tubes (Comardo) or groups of tubes (Johns, et al.). Both of these catalyst tube blow-down and Delta P or back-pressure testing systems are based on the need for efficiency of catalyst tube testing, and the testing of each of the multitude of reactor tubes of a typical tube and shell type catalytic reactor. The multi-tube blow-down and D-P testing apparatus covered by U.S. Pat. No. 6,694,802 Comardo achieves individual testing of each reactor tube and thus provides a test report providing the actual test results of each tube. The apparatus of Johns, et al. conducts simultaneous tests on groups of reactor tubes and thus achieves averaging of the back-pressure for the tubes of each test group. Thus some tubes may test high and others may test low, with the averaged and recorded test measurement perhaps indicating an optimum back-pressure, indicating optimum reactor tube loading, when such may not be the case.

SUMMARY OF THE INVENTION

It is a principal feature of the present invention to provide a novel method and apparatus for mechanized and electronically controlled testing of groups of catalyst filled reactor tubes of a tube and shell type catalytic reactor and providing back-pressure responsive electronically generated test data for each reactor tube and to record the test data in electronic form and/or computer print-out form as a permanent record for the reactor owner.

It is another feature of the present invention to provide a novel method and apparatus for conducting blow-down and/or back-pressure tests of groups of reactor tubes by utilizing one or more mobile test units that are located within a reactor shell and on the upper tube sheet of the reactor and are moved linearly on the upper tube sheet and in controlled manner to accomplish sequential back-pressure testing of reactor tubes according to a numerical code or other tube identification system of the reactor and to transmit electronic back-pressure test data to an integrated computer that processes the test data and produces an electronic record of the back-pressure test of each of the multitude of reactor tubes of the reactor.

It is another feature of the present invention to provide a novel method and apparatus for conducting blow-down of reactor tubes in a manner by-passing the usual back-pressure orifice and thus permitting a maximum allowable volume of air or other blow-down gas to be injected into the reactor tubes for removal of any dust that might be present therein.

It is also a feature of the present invention to provide a novel method and apparatus for conducting blow-down and/or back-pressure tests of groups of reactor tubes of a tube and shell type catalytic reactor and which has the capability of selectively electronically counting both in normal testing sequence and in inverted testing sequence to accommodate the movement direction and the orientation of the testing cart or carts relative to the upper tube sheet of the reactor and to accurately correlate the back-pressure tests of the reactor tubes with the numerical or other code tube identification system of the reactor so that the back-pressure test of each reactor tube is specifically identified and recorded.

It is also a feature of the present invention to provide a novel method and apparatus for accomplishing multiple tube testing of the reactor tubes of a catalytic reactor which permits identification and sequential recording of disabled reactor tube positions due to plugged tubes or the presence of thermocouple or other sensing devices in selected reactor tube openings of the upper tube sheet of a reactor.

It is also a feature of the present invention to provide a novel method and apparatus for conducting blow-down and/or back-pressure tests of groups of reactor tubes of a tube and shell type catalytic reactor and which incorporates selectively used and actuated manual back-pressure test mechanisms to accomplish efficient DP testing of reactor tubes that, because of their location within a reactor, are difficult or virtually impossible to test with a multiple tube testing cart.

It is also a feature of the present invention to provide a novel method and apparatus for conducting blow-down and/or back-pressure tests by employing one or more mobile test units having wheels for mobility and with at least one of the wheels being employed to drive a linear encoder and to cause activation of encoder activated position indicating lights or other signal devices to indicate proper positioning of the mobile test unit with respect to the reactor tubes of a particular row of reactor tubes.

It is an even further feature of the present invention to provide a novel method and apparatus for conducting blow-down and/or back-pressure tests of groups of reactor tubes of a tube and shell type catalytic reactor and which minimizes the servicing time and labor that is ordinarily required during reactor servicing operations and permits the use of relatively unskilled reactor service labor for testing and data recording activities.

It is a feature of the present invention to provide a novel method and apparatus for conducting blow-down and/or back-pressure tests of groups of reactor tubes of a tube and shell type catalytic reactor wherein one or more testing carts are located within a reactor shell and on the upper tube sheet of the reactor and are each provided with a moveable test probe array including plurality of moveably mounted test probes that are positioned according to reactor tube spacing to engage and seal with respective reactor tubes and apply gas pressure into the reactor tubes for back-pressure tests and wherein a single control unit may be located either internally or externally of the reactor shell and is coupled with each of the mobile test units by a suitable system for conducting pneumatic pressure and electrical power and control signals to the mobile test units and for receiving, processing and recording electronic data from the mobile test units.

It is also a feature of the present invention to provide a novel method and apparatus including one or more mobile test units for conducting blow-down and/or back-pressure tests of groups of reactor tubes of a tube and shell type catalytic reactor and with each of the mobile test units having an independently useable testing wand that permits efficient testing of reactor tubes that cannot be accessed by the multiple tube testing apparatus of the mobile test units.

It is a further feature of the present invention to provide a novel method and apparatus for conducting blow-down and/or back-pressure tests and employs one or more wheel mounted mobile test units each having a vertically moveable array of test probes and with the array of test probes also being selectively laterally moveable relative to the mobile test unit for access to reactor tubes that may be located near the reactor shell wall or in other tight areas that might otherwise be difficult to reach and test.

Briefly, the objects and features of the present invention are realized through the provision of a differential pressure testing system that accomplishes blow-down and testing of each of the multiplicity of catalyst containing reactor tubes of a tube and shell type catalytic reactor and provides a permanent electronic and or hard copy record of the test of each of the reactor tubes, thereby enabling the owner or operator of the reactor to determine at any given point in time if the reactor is performing properly or if it is in need of cleaning and catalyst changing in order to meet desired performance standards.

Though not limiting, the invention may be practiced by locating on the upper tube sheet of the reactor at least one and preferably a plurality of mobile test units, with each of the mobile test units connected by an electrical, computer network and pneumatic umbilical with a control unit which is preferably located off to the side of the upper tube sheet or plate of the reactor or located externally of the reactor shell. A single mobile test unit is shown in the drawings but it should be understood that several mobile test units (typically four for a large reactor) may be used if desired. Though a single control unit is shown, more than one may be utilized, each having umbilical connection with one or more mobile test units.

The control unit contains a computer having a memory system and also includes a computer driven printer which produces a hard (paper) copy of test data for all of the tubes of the reactor. The computer memory may be downloaded to a larger, permanent memory system if desired and/or may be permanently recorded on a compact disk or other suitable memory device, so that the test data may be available for comparative use with subsequently acquired test data if desired or used in any manner that benefits the reactor owner or reactor service contractor. The control unit has connections for compressed air or other test gas under pressure and for electrical power, typically 12 Ov A/C. Electrical, ethernet computer conductors and pneumatic conductors are provided in an umbilical cable for each of the mobile test units and are received by umbilical connections of the control unit.

For blow-down of the reactor tubes prior to differential pressure testing, the orifice that is employed for pressure and volume control during differential pressure testing is bypassed, thereby allowing a high volume of air to be injected into a reactor tube for removal of dust and other debris that may be present therein as the result of catalyst loading. Also, during differential pressure testing each reactor tube is independently tested and a test record is achieved for each reactor tube so that management can decide to remove the catalyst, refill the reactor tubes that test unusually high or low. The computer and computer program also achieve recording of test data for the individual reactor tubes in colors, such as green for reactor tubes having a back-pressure within a desired range, red for reactor tube back-pressure above the desired range and yellow for reactor tube back-pressure below the desired range. These color coded test reports provide management with easily recognized test documentation that identifies the back-pressure of individual reactor tubes. Thus out of range test results are easily seen simply by scanning a print-out or the computer screen immediately upon completion of differential pressure testing. Moreover, the quality of the reactor service procedure is clearly evident. If further reactor servicing should be done to improve the quality of spent catalyst removal, reactor tube cleaning and loading, this work can be done while the reactor service personnel are on site and immediately available for the work.

Since tube and shell type catalytic reactors are typically of circular cross-sectional configuration and many of the reactor tube openings of the tube sheets are located close to the inner wall surfaces of the reactor shell, it is often difficult to position reactor tube loading equipment and reactor tube testing equipment so that some of the loading or testing probes can be positioned in registry with these tubes. To accommodate situations where the reactor tube openings are located in tight spots, it is desirable to provide a mobile testing unit, such as a mobile test unit having a laterally moveable testing manifold having thereon an array of test probes. After the mobile testing unit has been positioned as close as possible to the tubes that are difficult to access, the laterally moveable testing manifold can be shifted laterally in controllable manner to bring at least some of the testing probes into registry with the otherwise inaccessible reactor tube openings. The mobile testing unit is also provided with a manually positioned testing wand, thereby providing service personnel with the capability of testing reactor tubes that are difficult to access.

At times, for access to reactor tube openings by the multiple testing probes of the testing manifold, it becomes necessary to reverse the position of the mobile testing unit and to move it in the opposite linear direction during the tube testing procedure for certain rows of reactor tubes. To accommodate this situation and to ensure that the test results of these rows of tubes appear in proper order in reactor test reports, the computer program permits the arrangement of test data to be inverted or reversed with respect to the order of test data acquisition. Thus, regardless of the direction to movement of the mobile testing unit during successive tests, the resulting reactor test report will display the test results of each reactor tube according to the reactor identification system.

BRIEF DESCRIPTION OF THE DRAWINGS

So that the manner in which the above recited features, advantages and objects of the present invention are attained and can be understood in detail, a more particular description of the invention, briefly summarized above, may be had by reference to the preferred embodiment thereof which is illustrated in the appended drawings, which drawings are incorporated as a part hereof.

It is to be noted however, that the appended drawings illustrate only a typical embodiment of this invention and are therefore not to be considered limiting of its scope, for the invention may admit to other equally effective embodiments.

IN THE DRAWINGS

Figure 1:
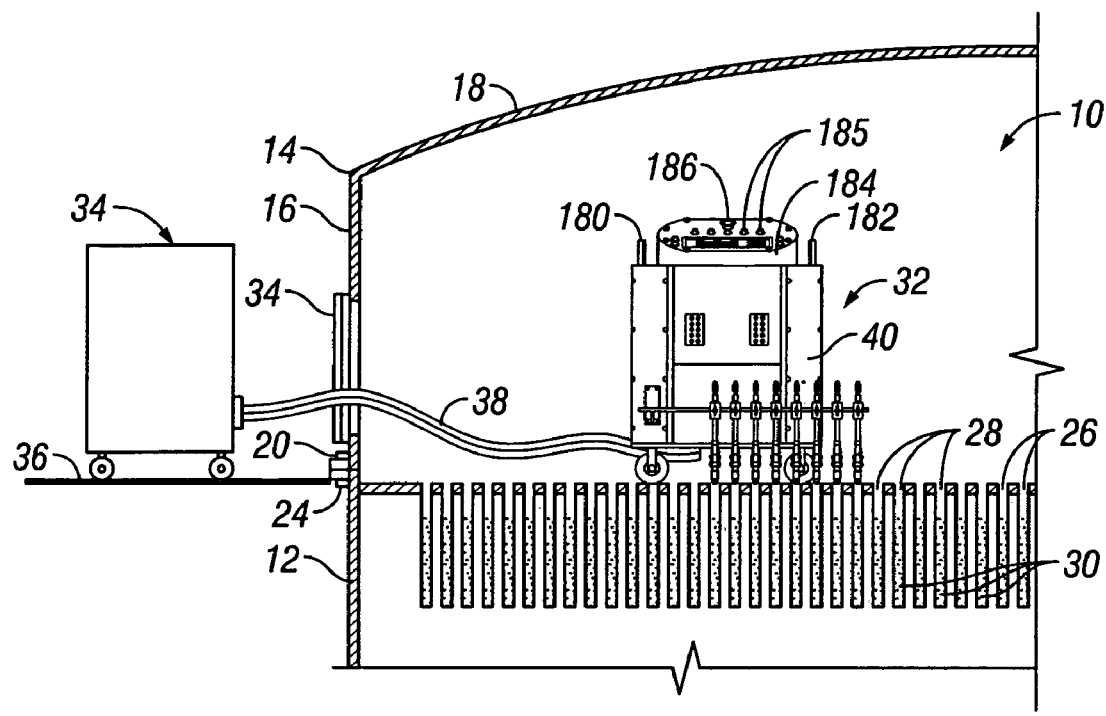
Figure 2:
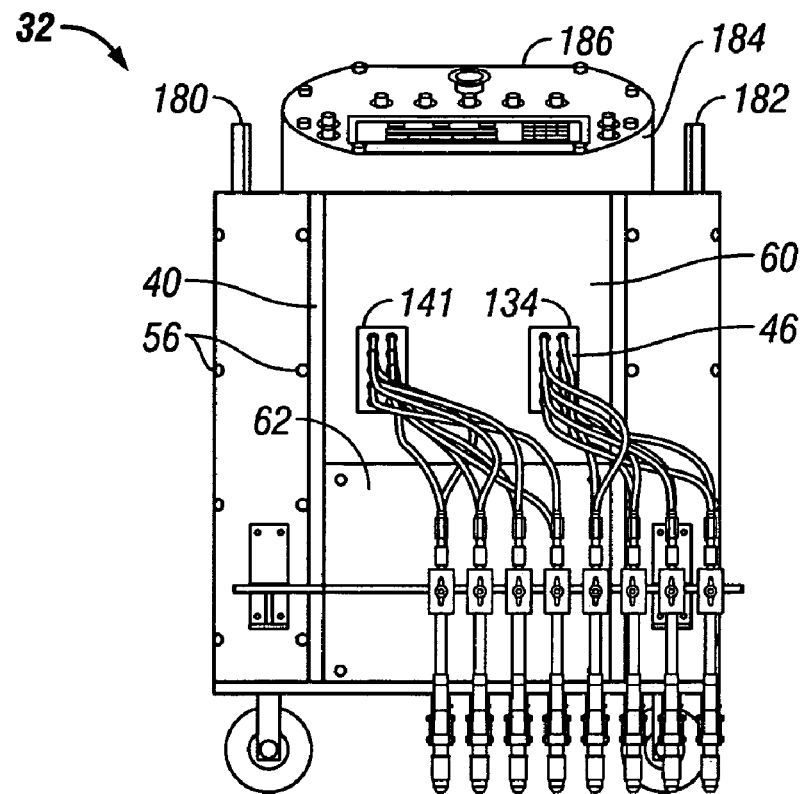
Figure 3:
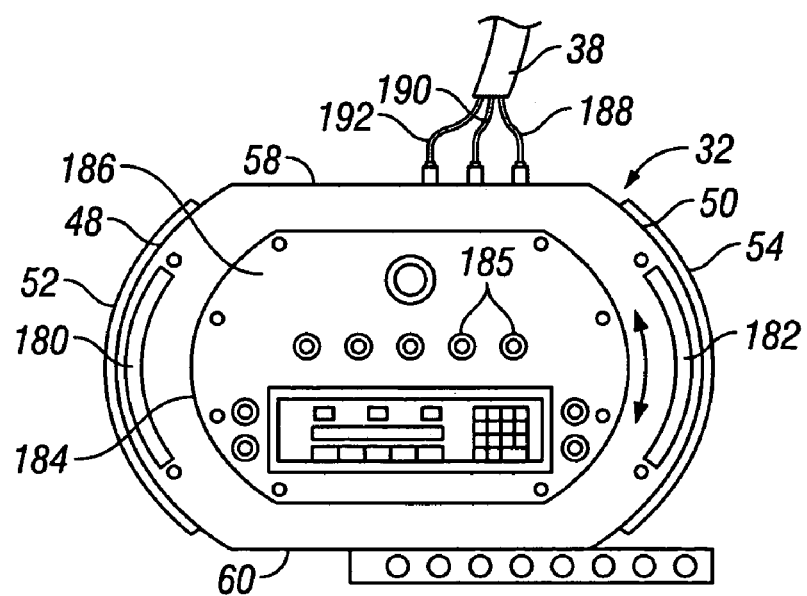
Figure 4:
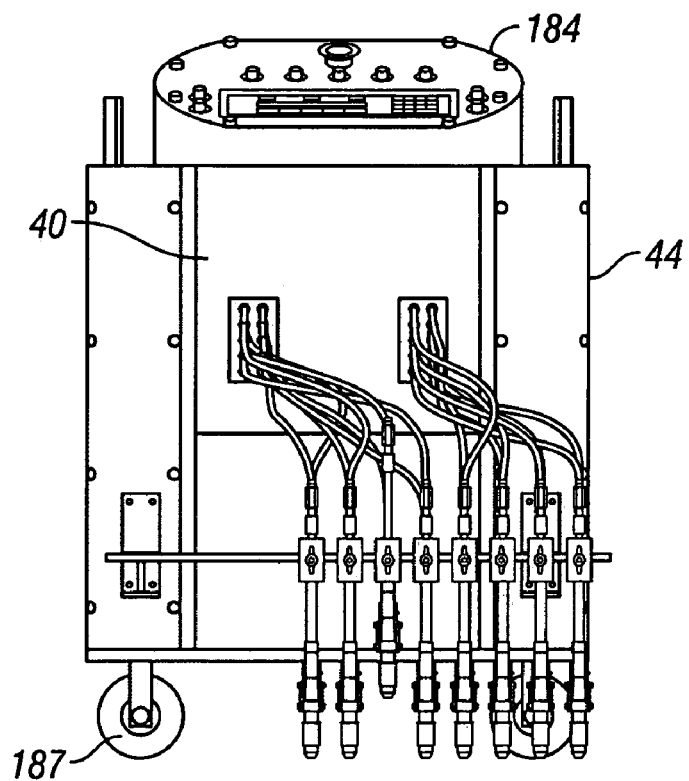
Figure 5:
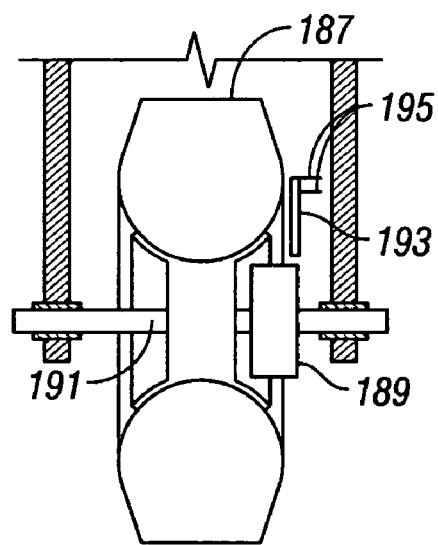
Figure 6:
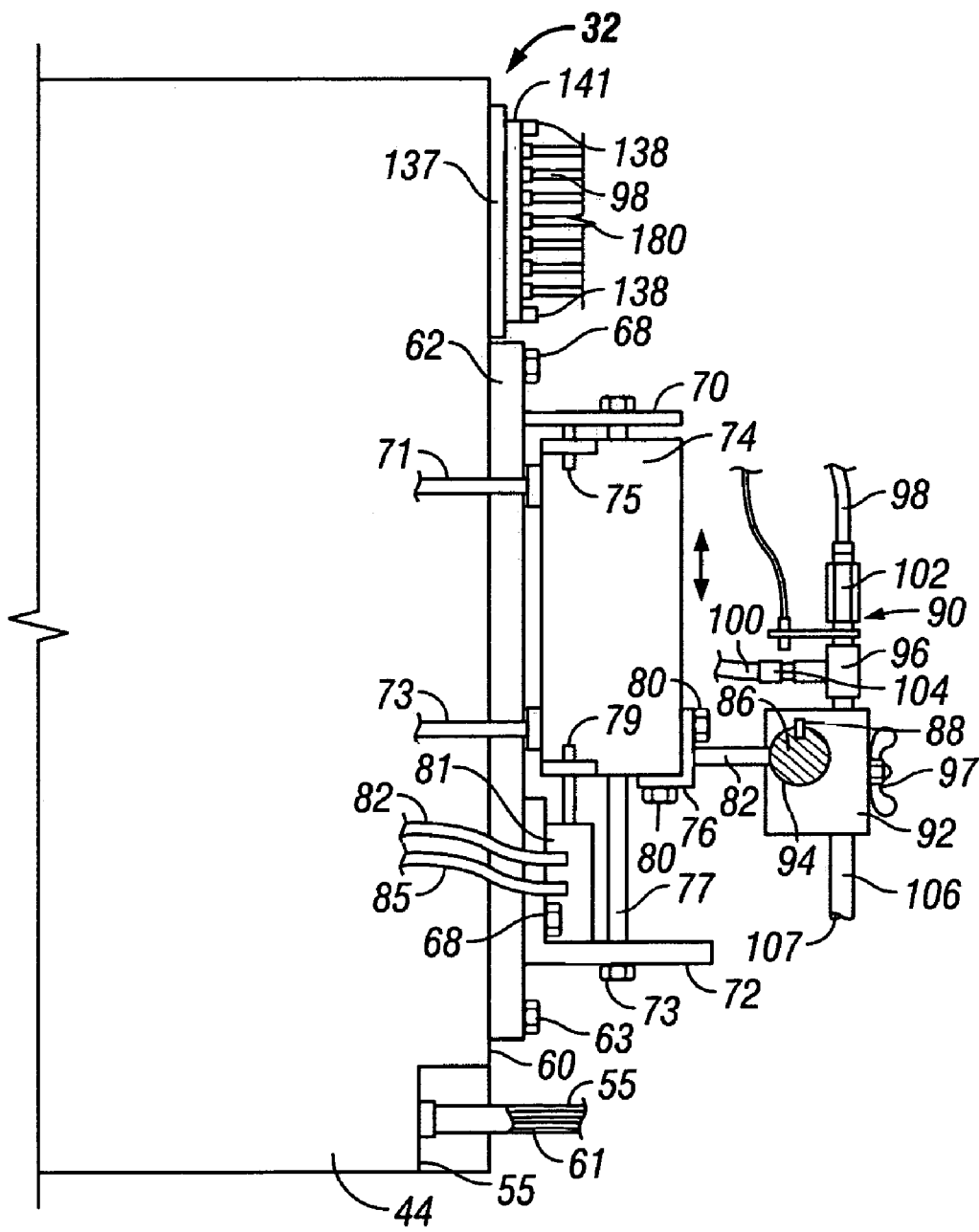
Figure 7:
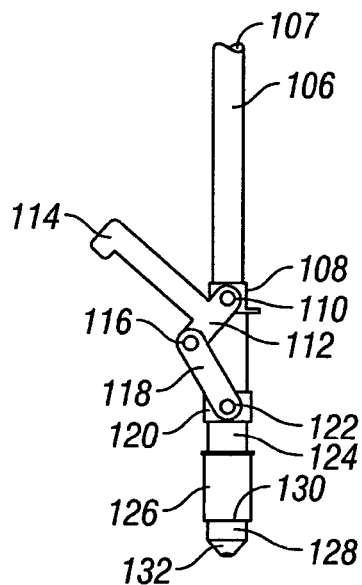
Figure 8:
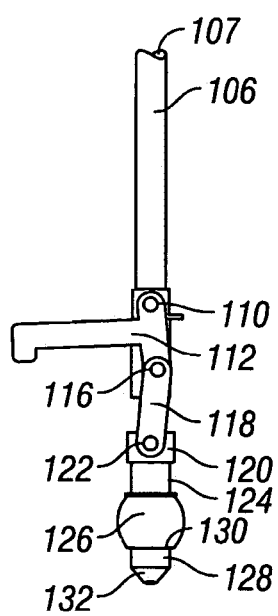
Figure 9:
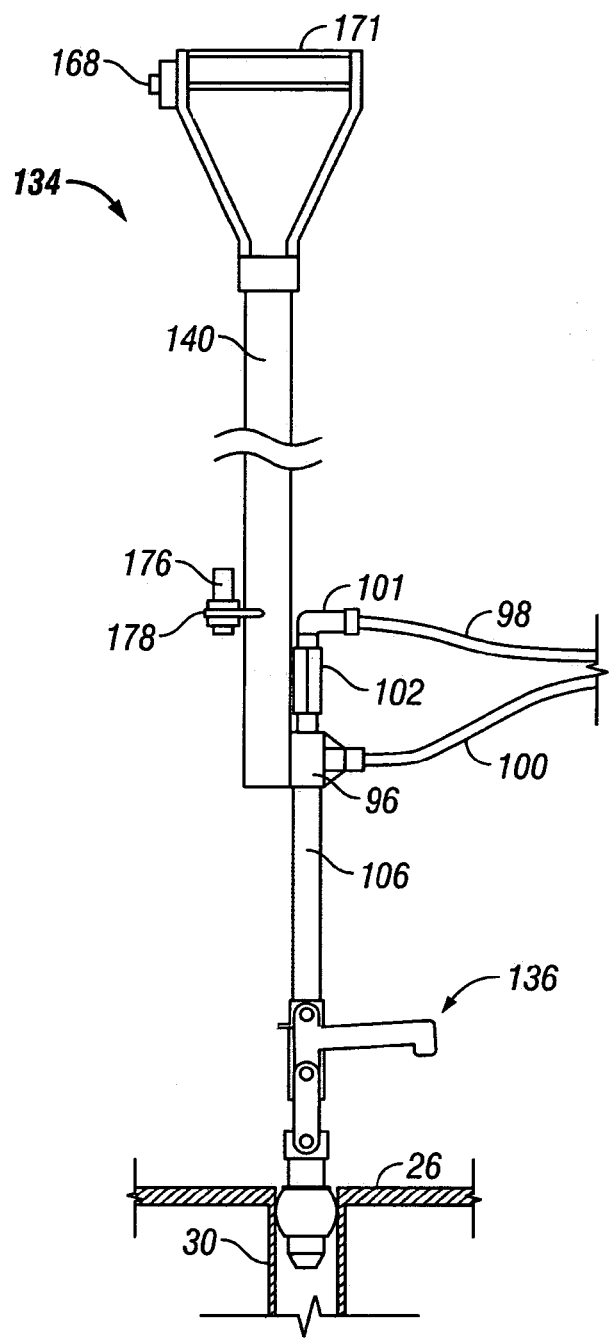
Figure 10:
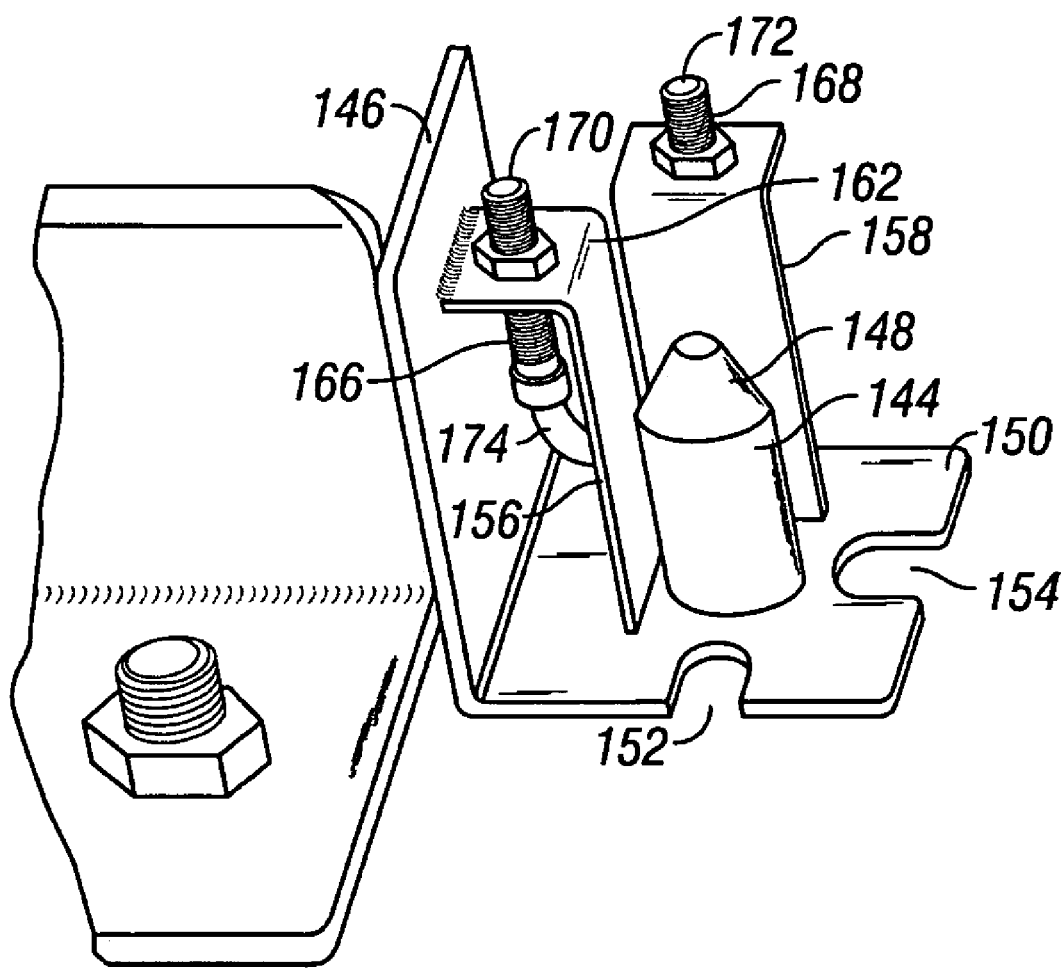
Figure 11:
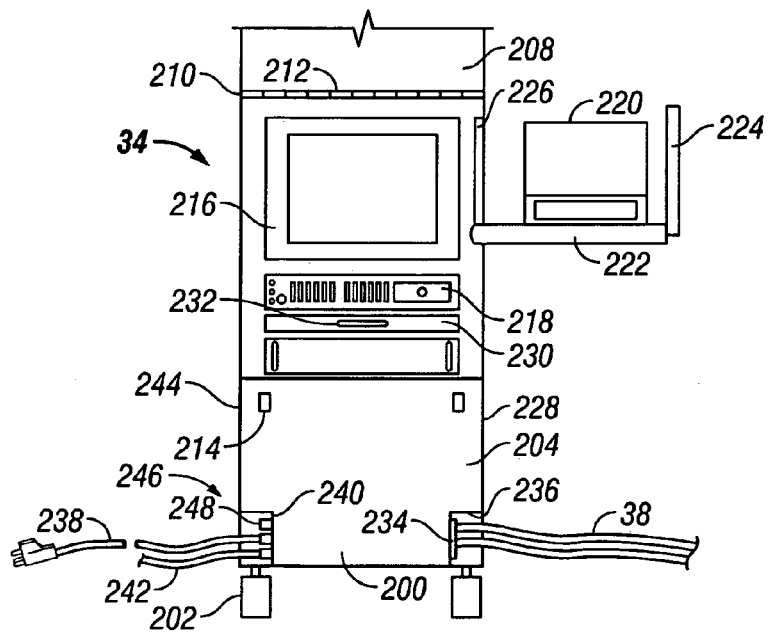
Figure 12:
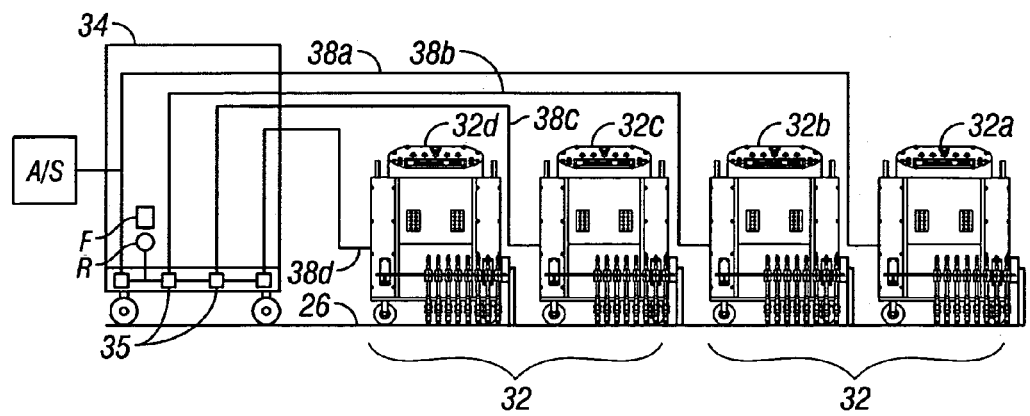
Figure 13:
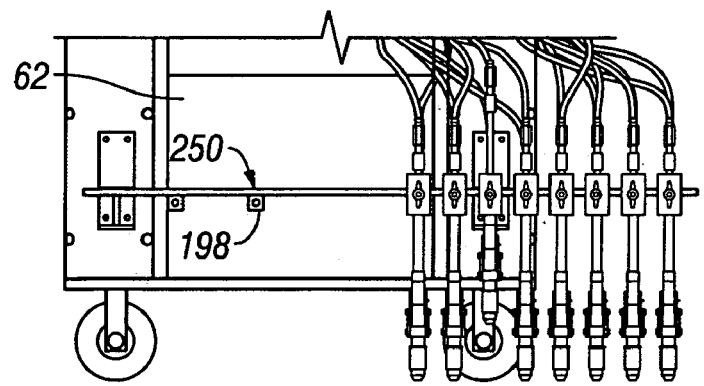
Figure 14:
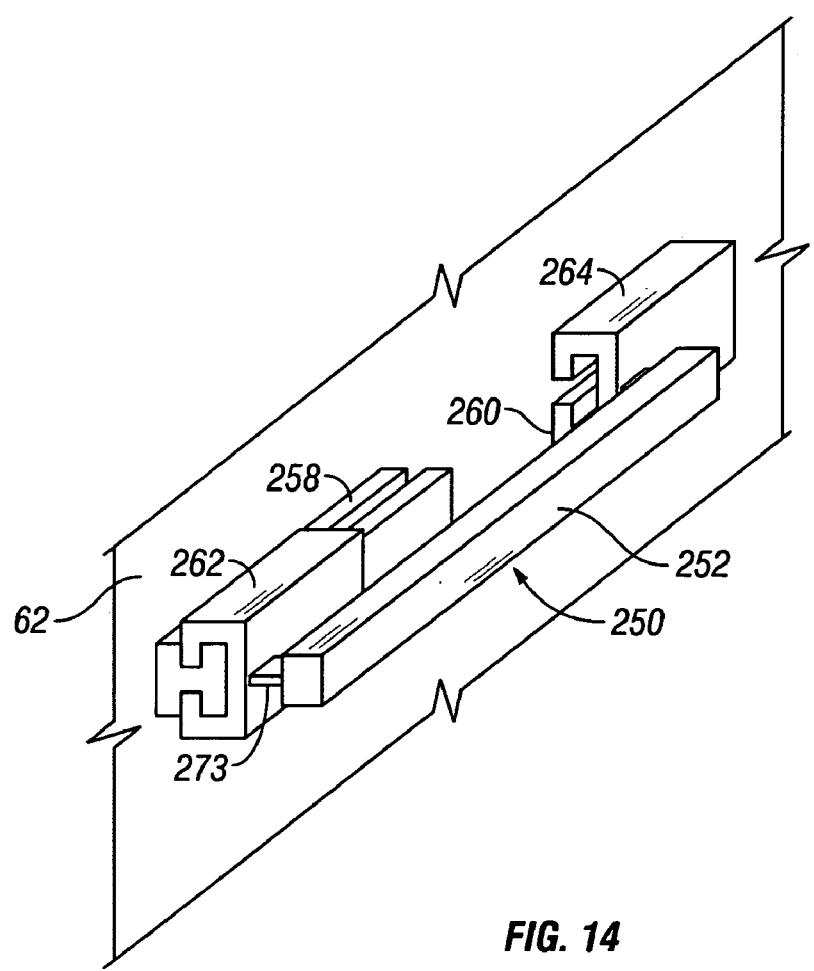
Figure 15:
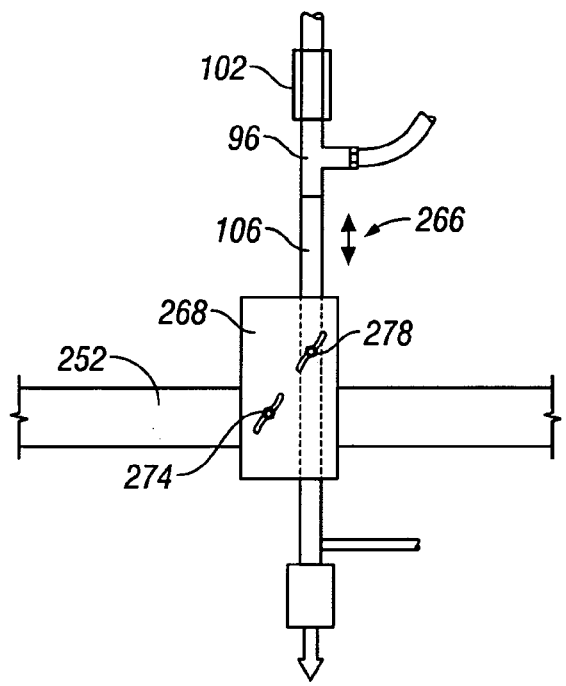
Figure 16:
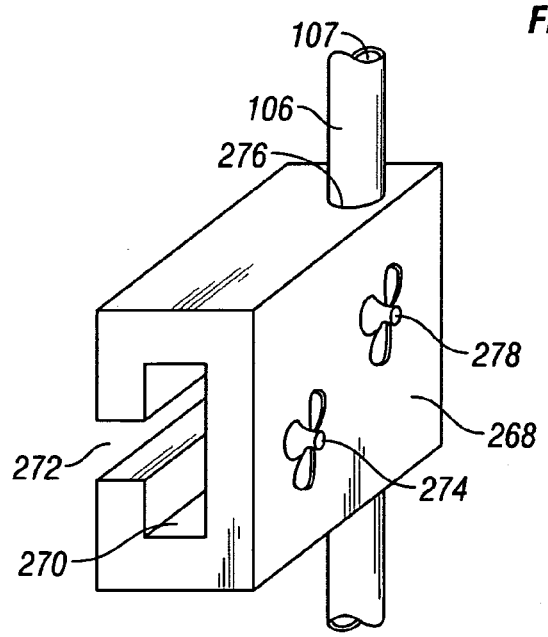
Figure 17:
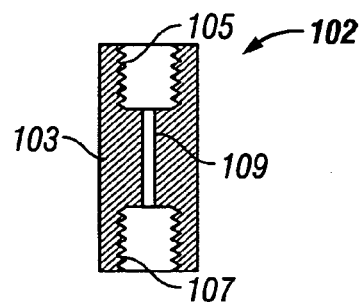
Figure 18:
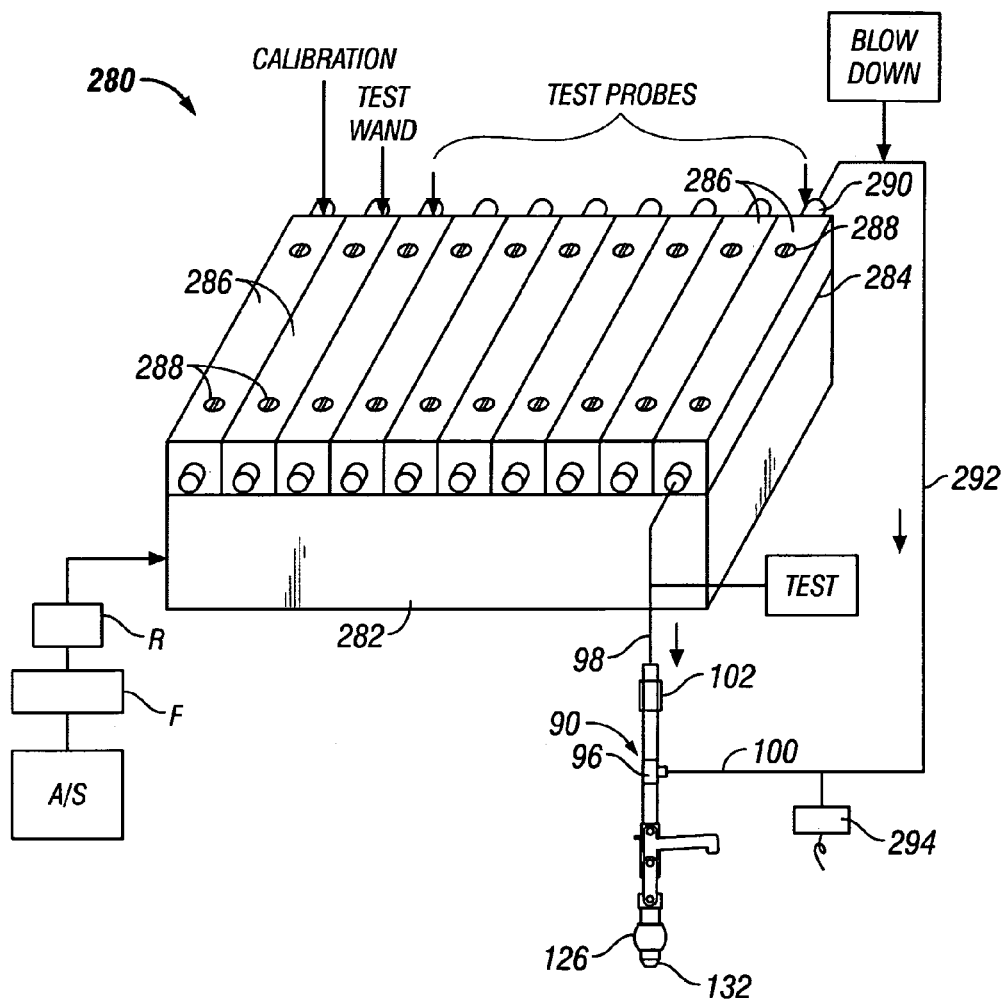
Figure 19:
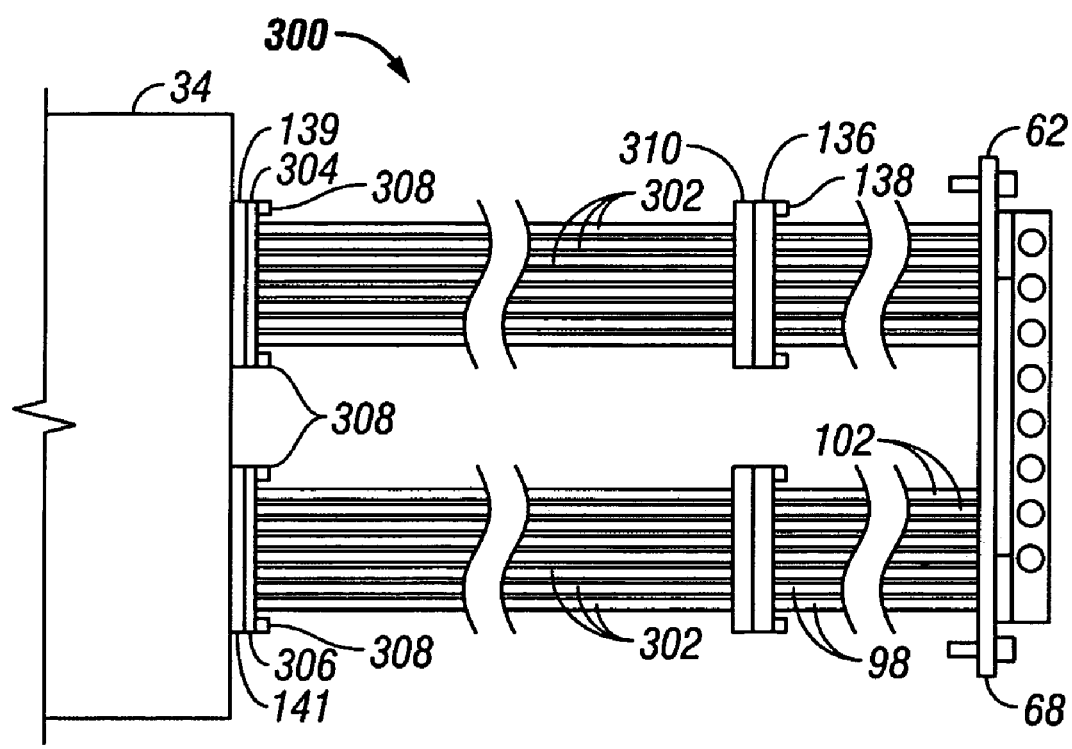

FIG. 1 is a pictorial illustration in elevation, showing an upper portion of a tube and shell type catalytic reactor and showing a portion of the upper tube sheet of the reactor, and with a DP mobile test unit located within the reactor shell and on the upper tube sheet and also showing a control unit located externally of the reactor shell and being coupled with the DP mobile test unit by an umbilical for electrical supply, electronic signal transmission and pneumatic supply;

FIG. 2 is an elevational view showing a mobile test unit that is constructed in accordance with the principles of the present invention;

FIG. 3 is a plan view showing the upper portion of the mobile test unit of FIGS. 1 and 2;

FIG. 4 is an elevational view showing the lower portion of one of the mobile test units and showing the test probe manifold of the mobile test unit with one of the test probes thereof being retracted for accommodation of a disabled reactor tube position, such as when a plug or thermocouple is present at a reactor tube position;

FIG. 5 is a partial sectional view showing a wheel actuated encoder system for actuating position indicating lights on the rotatable inspection pedestal of the mobile test unit to confirm linear positioning movement of the mobile test unit to sequentially register its test probe array with a next group of reactor tubes to be tested;

FIG. 6 is a side elevational view showing a part of the mobile test unit of FIG. 2 and showing the upwardly and downwardly moveable test probe manifold thereof being located at its upward position and further showing a portion of one of the test probes thereof in detail;

FIG. 7 is an elevational view showing a lower portion of a test probe of the mobile test unit of FIGS. 1 and 2, with the seal actuating toggle mechanism thereof being shown in its released or non-sealed position;

FIG. 8 is an elevational view similar to that of FIG. 6 and showing the seal actuating toggle mechanism of the test probe in its activated or sealed position for expanding a resilient sealing element and sealing the test probe within a catalyst tube opening;

FIG. 9 is an elevational view showing the manually operable DP test wand that is provided on each of the control units and showing the resilient seal there of being located and sealed within a reactor tube by the toggle linkage actuation mechanism thereof;

FIG. 10 is an isometric illustration of a test wand support bracket assembly for supporting a test wand and for electronically confirming the active or inactive status of the test wand channel of the DP testing system;

FIG. 11 is a front elevational view of the control unit of FIG. 1, showing the opened condition thereof, with the printer tray of the control unit open to permit access to the printer and showing the keyboard tray, computer module and monitor of the control unit exposed for viewing by a reactor service worker;

FIG. 12 is a schematic illustration showing a control unit and a plurality of mobile test units, with umbilicals interconnecting the control unit with each mobile test unit for electrical power, pneumatic supply and computer interface;

FIG. 13 is an elevational view showing a lower portion of an alternative embodiment of the present invention wherein a mobile test unit is shown having a test probe array that is mounted for selective lateral movement relative to the mobile test unit to enable lateral positioning of the test probe array thus enabling test probe access to and testing of reactor tubes that may not be readily accessible by the test probes of the mobile test unit;

FIG. 14 is an isometric illustration showing a part of the front wall of a control unit and with a slide bearing mounting system to which an array support bar is mounted to permit selective lateral movement of the test probe array as shown in FIG. 13 to gain access to reactor tube positions near reactor shell walls;

FIG. 15 is a front elevational view showing one of the test probes and illustrating vertical test probe positioning to accommodate inactive reactor tube positions having thermocouples or plugs and illustrating lateral test probe positioning for test probe pitch adjustment to accommodate the pitch, i.e., spacing, of the reactor tubes of a particular catalytic reactor;

FIG. 16 is an isometric illustration showing the configuration of the guide block in detail and showing the relationship of the tubular member of a testing probe to the guide block;

FIG. 17 is a sectional view of the coupler/orifice member of the test probe of FIGS. 2, 4, 6 and 15, showing the structure thereof in detail;

FIG. 18 is a schematic isometric illustration showing the control valve assembly of a mobile test unit for selectively achieving blow-down and differential pressure testing of a plurality of reactor tubes via a testing manifold having a plurality of test probes; and FIG. 19 is a partial elevational view in schematic form, showing an alternative embodiment of the present invention enabling the test probe array of the differential pressure reactor tube testing system to be separated from its testing unit and used for conducting differential pressure tests of reactor tubes that may be difficult to access with the test probe array in assembly with the testing unit.

DETAILED DESCRIPTION OF PREFERRED EMBODIMENT

Referring now to the drawings and first to FIG. 1, a tube and shell type catalytic reactor is shown generally at 10 and incorporates a pressure containing reactor shell comprised of a reactor wall 12 that is typically of cylindrical configuration and a reactor dome 14 having a dome wall 16 and a curved upper dome wall 18. The reactor dome is provided with a mounting flange 20 which establishes sealing engagement with a support flange 22 of the reactor wall 12. Bolts or threaded studs and nuts 24 are employed to secure the flanges 20 and 22 in sealed assembly. Upper and lower tube sheets are mounted transversely of the reactor wall 12, the upper tube sheet 26 being shown in FIG. 1. The upper and lower tube sheets define a multiplicity of holes 28 within which the respective upper and lower ends of reactor tubes 30 are typically connected by welding. As mentioned above, a large tube and shell type catalytic reactor may have 20,000 to 80,000 reactor tubes, more or less, each containing catalyst pellets for reaction with a process fluid that is passed through the reactor tubes. After spent catalyst has been removed from the reactor tubes and the tubes have been cleaned during a reactor servicing operation, the reactor tubes will be loaded with fresh catalyst, which is typically in pellet form. Though the reactor tubes can be loaded one at a time, present day catalyst servicing operations are typically conducting by using a mechanized and computer controlled catalyst loading equipment of the type shown in U.S. Pat. Nos. 5,890,868 and 5,897,282 of Mathis P. Comardo. This mechanized catalyst loading equipment achieves catalyst loading at a predetermined drop rate that is determined by the size and length of the reactor tubes, the size and density of the catalyst pellets, so that each of the multiplicity of reactor tubes is loaded in substantially identical fashion. When properly loaded with catalyst, all of the reactor tubes of the reactor will exhibit substantially identical backpressure when subjected to DP testing, unless some other factor has intervened. To ensure that the reactor has the capability for optimum process reaction efficiency, any of the reactor tubes that exhibit unusually high or low backpressure should be cleaned of catalyst and then re-loaded.

Though the reactor tubes can be subjected to DP testing one at a time, if all of the reactor tubes are to be tested the time and labor requirements for reactor turn-around (cleaning, re-charging and testing of the reactor tubes) would typically be commercially undesirable. Thus, according to the teachings of U.S. Pat. No. 6,694,802 and according to the present invention, one and preferably a plurality of mobile test units shown generally at 32 are introduced into a reactor shell through a man-way 34 of the reactor dome 14. Personnel for conducting the reactor tube testing operation will also enter the reactor shell via the man-way and will operate the mobile test units on the upper tube sheet 26 for controlled sequential testing of each or the reactor tubes 30 to identify the back-pressure thereof. These mobile test units are also employed to accomplish blow-down of the reactor tubes, assuming that the servicing protocol calls for blowing the reactor tubes with a gas such as compressed air at the start of a test procedure, to clear the reactor tubes of catalyst dust and other debris that might otherwise interfere with desired flow of process fluid.

A single control unit or cart shown generally at 34 is typically located externally of the reactor shell, such as being supported by a service platform 36. Each of the mobile test units is provided with an umbilical 38 for coupling a mobile test unit 32 with the control unit 34 electrically for power, electronically for signal transmission and pneumatically for pneumatic fluid supply. The umbilical 38 is flexible and is of sufficient length to permit movement of the control unit to any desired position on the upper tube sheet 26 within the reactor shell.

Referring now to FIGS. 2 and 3, each of the mobile test units 32 have a cart housing 40 which is moveably supported on the upper tube sheet 26 of a reactor by a plurality of wheels 42. Preferably, for purposes of controlling desired movement of the mobile test units on the upper tube sheet, the wheels 42 are not casters, but rather are arranged to essentially limit the mobile test unit to linear movement along the surface of the upper tube sheet for the reason that the reactor tubes are arranged in staggered rows to maximize the number of reactor tubes that are possible for tube sheets of a given reactor dimension. However, it is not intended to limit the present invention to the use of wheels of any specific character, it only being necessary that mobile test unit be capable of movement on the upper tube sheet to enable positioning of the multiple test probes of the mobile test unit into simultaneous sealed engagement within a selected group of linearly arranged reactor tube openings of the upper tube sheet.

Each mobile test unit 32 is provided with a cart housing 44 which is essentially hollow thus defining an internal compartment 46 within which electrical and pneumatic hardware is located. The cart housing 44 defines at least one and preferably two opposed access openings 48 and 50 which are normally closed by curved housing closure panels 52 and 54 that are each secured to the housing structure by a plurality of panel retainer screws 56. The cart housing 44 defines at least one and preferably a pair of generally planar wall sections or panels 58 and 60.

A mounting plate 62 of generally planar rectangular configuration is mounted to the wall section or panel 60 by threaded mounting studs that project from the wall panel 60 and by retainer nuts that secure the mounting plate to the mounting studs. It should be borne in mind that the mounting plate is removably fixed to the cart housing and that for purposes of handling and transportation of the mobile test unit the mounting plate, with the entire test probe manifold assembly attached thereto, is removed and placed within a suitable protective shipping container. Likewise, assembly of the test probe manifold assembly to a cart housing is accomplished simply by assembling the mounting plate to the threaded studs and tightening lock nuts on the threaded studs.

As further shown in FIG. 6 each mobile test unit housing 44 defines at least one external housing recess 55 within which is located a female electrical connector receptacle 57 which is fixed into the wall structure of the housing. The connector receptacle 57 provides for releasable electrical coupling of a number of limit switch power and control conductors, there being a limit switch power conductor and a limit switch control conductor for each of the test probes of the testing array of each testing unit or cart and a limit switch power conductor and a limit switch control conductor for the testing wand. Limit switch power and control conductors are also provided for the linear actuators for the test probe array. As an example, the female electrical connector receptacle 57 is provided with connector pin openings for at least 22 individual circuits. A male electrical connector member 59 defines the connecting end of a limit switch power and control cable 61 having multiple limit switch power and control conductors and is provided with multiple connector pins, there being one connector pin for each of the connector pin openings of the female electrical connector receptacle 57. The male electrical connector member 59 is designed for releasable locking engagement with the electrical connector receptacle 57. In FIG. 6, to facilitate understanding of the invention, the male electrical connector member 59 is shown separated from the female electrical connector receptacle 57, but it is readily understood that these connector components are in assembly when the testing units and disposed in operative assembly with the control unit.

Pairs of cylinder mounting brackets 64 and 66 are retained in assembly with and on opposed sides of the mounting plate 62 by mounting bolts 68 and have spaced cylinder mounting flanges 70 and 72 that provide support for a pair of laterally spaced cylinders or linear pneumatic motors 74 and 76. The cylinders 74 and 76 are each linearly moveable relative to a piston rod 77 responsive to application of pneumatic pressure to either side of an internal piston thereof. Pneumatic pressure is supplied and returned by pneumatic tubes 71 and 73 under the control of an actuator valve of the pneumatic circuitry of the system for raising and lowering the test probe array relative to the housing of the mobile test unit. These pneumatic supply and return tubes extend from plug-in type quick disconnect modules which will be discussed in detail below. Piston actuation is achieved pneumatically, responsive to actuation of an electrical selector or switch that controls the operation of a solenoid valve in the pneumatic supply to the cylinder actuators. The piston rod 77 of each piston is fixed at respective ends thereof to the cylinder mounting flanges 70 and 72 by means of nuts 73 or other retainer members. To identify the position of the pneumatic actuators and thus ensure desired positioning of the moveable test probe array, at least one of the linear actuators is provided with at least one limit switch, preferably a magnetically actuated limit switch. Adjustable switch actuators 75 and 79 are mounted on brackets and achieve actuation of a magnetically actuated limit switch 81. When the limit switch is actuated an electrical circuit including switch conductors 83 and 85 provides an electronic signal to the computer of the control unit that confirm the position of the linear actuators and thus the moveable test probe array that is in fixed relation with the actuators.

A pair of laterally spaced support brackets 76 and 78 are fixed to the operator cylinders 74 and 76 by means of mounting bolts 80 and have guide bar support members 82 and 84 fixed thereto and projecting laterally therefrom. The guide bar support members are each fixed, such as by welding to an elongate, straight guide bar 86 that is oriented substantially horizontally. The guide bar 86 may be of circular cross-sectional configuration as shown in FIG. 6, though it may have any other desired cross-sectional form, such as, square, rectangular, as shown in FIG. 14, or octagonal configuration for example, without departing from the spirit and scope of the present invention. The guide bar 86 of FIG. 6 defines an elongate track or guide slot 88 that is of essentially rectangular cross-sectional configuration and opens upwardly. The guide bar arrangement shown in FIG. 14 and related figures will be discussed in detail hereinbelow in connection with these figures.

Each of a plurality of test probes, one being shown generally at 90, is provided with a guide block 92 located intermediate the length thereof. The guide block defines a circular opening 94 within which the guide bar is received in reasonably close fitting relatively moveable relation therein. A guide key is fixed to the guide block within the circular opening 94 and projects downwardly into the elongate track or guide slot 88, thus ensuring accurately controlled orientation of the guide block and thus the test probe 90. The guide block is linearly moveable to desired positions along the length of the guide bar 86 and is capable of being substantially locked to a selected immobile position on the guide bar by tightening of a wing-nut type locking bolt 97. This feature permits the pitch, i.e., spacing of the plurality of test probes to be adjusted and set to match the pitch of the reactor tube openings.

For pneumatic fluid supply to the test probes tee members 96 are threaded into or otherwise connected to each of the guide blocks 92. A pneumatic test pressure supply line 98 and a pneumatic blow-down supply line 100 are connected by a coupler/orifice member 102 and a coupler member 104 to the tee member 96. Coupler/orifice member 102 is shown in detail in FIG. 17 and is defined by a coupler/orifice body 103 having internally threaded ends 105 and 107 for connection with the tee member 96 and for connection with the testing and blow-down air supply. The coupler/orifice member 102 defines a small diameter orifice passage 109 that functions as an internal orifice of predetermined dimension which limits fluid flow from the supply line into the tee member and at a given air supply pressure permits a designed test pressure to be developed downstream of the orifice. The dimension of the orifice passage 109 controls the test pressure and volume that is used for differential pressure testing of the reactor tube that is engaged by the respective test probe 90. Obviously, the test pressure and volume can be changed to coordinate the testing capability of the testing system with the particular reactor simply by replacing the coupler/orifice member 102 with a coupler/orifice member having a larger or smaller diameter orifice passage. The pneumatic test pressure supply line 98 of each test probe extends from a respective test/blow-down valve which is shown in detail in FIG. 18.

The test/blow-down valve, the pneumatic test pressure supply line 98, the coupler/orifice member 102, the tee member 96 and the rigid tubular member 106 of each test probe collectively define a test flow path through which a predetermined test pressure is injected into a reactor tube being subjected to differential pressure testing. The test flow path, downstream of the coupler/orifice member 102 is in communication with a pressure sensor that detects the back-pressure that exists in the flow tee member 96 and the line 100 and converts the sensed back-pressure to an electronic signal that is in turn transmitted via the test unit/control unit umbilical 38 to the on-board computer of the control unit. The detected back-pressure is correlated to the specific reactor tube by the computer, according to its software, and is placed in memory for subsequent use in preparation of a computer generated record and printout or report of the test results of all of the tested reactor tubes of the catalytic reactor. The test/blow-down valve in its blow-down condition, the blow-down pressure supply line 100, the flow tee 96 and the rigid tubular member 106 of a respective test probe collectively constitute a blow-down flow path through which pressurized air is injected into respective catalyst filled reactor tubes for blow-down. The test/blow-down valve assembly of FIG. 18, as described in detail hereinbelow, is connected with a source of pressurized air, such as an air compressor or plant pneumatic supply line, which provides a supply of air which is typically above a predetermined desired blow-down pressure.

The printer of the control unit is a color printer and the computer software is capable of printing "in range" test results in a specified color, green for example, and is capable of printing "out of range—high" back-pressures in another color, such as red, and prints "out of range—low" back-pressures in a third color, such as yellow. The color-coded printout provides testing personnel and management with the capability to easily identify any reactor tube that tests high or low and to thus arrive at a conclusion that the reactor has been properly loaded with catalyst and is capable of providing quality process fluid. Alternatively, the color-coded test report can indicate that the reactor is not properly loaded and that remedial action is needed to render it capable of quality fluid processing. The tubes that test high or low are specifically identified and thus may be cleaned of catalyst, re-loaded and then may be re-tested to ensure that they are capable of optimum quality fluid processing.

It is desirable that blow-down of the catalyst filled reactor tubes be accomplished by injecting a relatively high volume of compressed air into the catalyst tubes to remove the dust that is typically present therein. As mentioned above, this dust can interfere with process fluid flow through the catalyst filled tubes and can interfere significantly with the processing quality capability of the serviced reactor. According to the features of the present invention, the orifice that controls test pressure is by-passed when blow-down is selected, thus admitting a large volume of air into the reactor tubes. When service personnel actuate the mobile test unit electronics to select blow-down, a test/blow-down valve, described in greater detail in connection with FIG. 18 is actuated to its blow-down position. The blow-down position of the valve opens in communication of the air supply and with the air injection passage of the test probe downstream of the restricted orifice and thus causes injection of compressed air at relatively high volume and pressure into a reactor tube. If desired, the blow-down valve may simultaneously isolate the back-pressure sensor when the blow-down valve is open.

After the test probes 90 have been adjusted for the particular pitch or spacing of the reactor tubes to be tested and their wing nuts 96 have been tightened to secure them in place, the cylinder actuators 74 and 76 will be actuated pneumatically, causing downward movement of the guide bar support member or members 82, thus simultaneously moving the array of test probes 90 downwardly and engaging the lower sealing ends of the test probes within a respective group of linearly arranged reactor tube openings. The test probes are then caused to establish sealing relation within the reactor tubes in preparation for blow-down and DP testing of the reactor tubes that are engaged. Sealing of the test probes within the reactor tubes can be accomplished simultaneously and by pneumatic control or the test probes may be individually actuated between non-sealing and sealing condition by mechanical actuation which may also be accomplished manually or by power actuation. As shown in FIGS. 6 and 7, the test probes, whether simultaneously actuated as a DP testing array or actuated individually as an independently positioned and actuated test wand as shown in FIG. 5, are preferably manually actuated for accomplishing sealing thereof within the reactor tubes and for release of sealing engagement. It should be borne in mind however that the test probes may be sealed or sealing thereof may be released in any suitable mechanized fashion.

Referring to FIGS. 6–8, the lower portions of the mechanized test probes 90 of FIG. 5 as well as the independently positioned and actuated test wand of FIG. 8, have a tubular, substantially rigid tubular member 106 which defines an internal flow passage 107 and has a linkage mount member 108 fixed thereto. A pivot 110 is provided on the linkage mount member 108 and provides pivotal support for an actuator link 112. The actuator link is of essentially L-shaped configuration and defines an actuating lever 114 that may be moved manually, such as by an upward or downward force that is applied by a foot of a worker using the equipment. The actuator link 112 is an integral member having a pair of spaced link elements that are located on either side of the linkage mount member 108. A pair of second pivots 116 is provided on the actuating link 112 and provides for pivotal connection of another pair of links 118 that are in turn pivotally connected to a linearly moveable seal actuator member 120 by a third pivot 122. A tubular seal actuator member 124 is positioned about the tubular member 106 and is linearly moveable by the seal actuator member 120. The tubular seal actuator member 124 is disposed in actuating engagement with a resilient seal member 126 that is of generally cylindrical configuration and has an external diameter less than the internal diameter of a reactor tube, thus allowing it to be easily inserted into a reactor tube for testing. The lower end of the resilient seal member 126 is supported by a seal support member 128 that is fixed to the lower end of the tubular member 106. The seal support member 106 is typically threaded to the lower end of the tubular member 106 and defines an upwardly facing support shoulder 130 on which the resilient seal member is seated. The lower end of the seal support member is tapered as shown at 132 so that it will be guided easily into a reactor tube opening even when the test probe is not precisely in aligned registry with the tube opening. The seal support member also defines an internal flow passage in communication with the flow passage 107 of the tubular member 106 so that a gas, such as compressed air, is transmitted through the flow passage of the tubular member 106 and through the seal support member 128 into a reactor tube being subjected to DP testing.

As mentioned above, to ready a selected group of reactor tubes for DP testing, the mobile test unit 32 is manually positioned so that its array of test probes are positioned directly above the group of reactor tubes to be tested. Reactor service personnel will then actuate a switch, causing opening of a control valve and causing admission of compressed air to the spaced cylinder actuators or motors. The actuator cylinders then drive the guide bar 86 and the array of test probes 90 downwardly, causing each of the test probes to enter the respective reactor tubes. A limit switch will be actuated after the test probes have been moved downwardly to their test positions, thus deactivating the cylinder motors. At this point, assuming that the seal actuating mechanism is of the mechanically actuated type as shown in FIGS. 6–8, the operator worker will apply a downward force on the actuating lever 114, such as by pressing on it with the worker's foot, thus causing sealing actuation of the toggle linkage involving links 112 and 118. As the toggle linkage is moved manually from the release position shown in FIG. 6 to the sealing position shown in FIG. 7 the seal actuator member 120 will be driven downwardly and will cause downward movement of the tubular seal actuator member 124, thus applying compression force to the resilient seal member 126. The compression force causes the resilient seal member 126 to be expanded to its sealing condition as shown in FIG. 7. Expansion or bulging of the seal member 126 in this manner causes it to establish sufficient pressure tight sealing within the upper end of a reactor tube to prevent leakage of air during a DP test procedure.

When the toggle linkage has reached the position shown in FIG. 7, it should be noted that the second or intermediate pivot 116 will moved over-center so that it will have crossed an imaginary line between the upper or first pivot 110 and the lower or third pivot 122. By moving the intermediate pivot over-center in this manner, the toggle linkage will have become mechanically locked and will retain the seal member in its expanded and sealing condition. Thus, the toggle linkage will maintain the sealing condition of the resilient sealing member until the toggle linkage is forcibly moved to the seal release position of FIG. 5. This can be easily accomplished by a worker, simply by applying a lifting force on the actuator lever 114 by lifting it with the worker's foot. Thereafter, the machine operator will then actuate the cylinder actuator switch to a test probe retraction position, causing the cylinder motors to move the guide bar 86 and the array of test probes upwardly, thereby extracting the test probes from the reactor tubes and readying the mobile test unit for linear movement on the upper tube sheet to a position for testing another group of aligned reactor tubes.

Since virtually all tube and shell type catalytic reactors are of circular cross-sectional configuration, to maximize the number of reactor tubes that are employed within a reactor shell of a given diameter, the reactor tubes are arranged in staggered rows, with the reactor tubes of each row being substantially equally spaced. Since the mobile test unit is provided with wheels that substantially restrict the mobile test unit to linear movement on the upper tube sheet, the mobile test unit can be oriented in substantially linear alignment with the orientation of a particular row of aligned reactor tube openings. Minor misalignment of the test probes with the reactor tube openings will be accommodated by the tapered ends of the array of test probes, which will guide the test probes into the selected group of reactor tubes. After D-P tests have been conducted on the selected group of reactor tubes, the array of test probes will be retracted clear of the reactor tube openings of the upper tube sheet. The worker will then move the mobile test unit linearly for blow-down and testing of the next group of reactor tubes, and so on until all of the reactor tubes of that particular row have been tested. The worker will then move the mobile test unit to the beginning of the next sequential row of reactor tube openings and will employ the same process from row to row until all of the reactor tubes have been tested. To permit all of the reactor tubes of a reactor to be tested in a short period of time the reactor tube openings, which are arranged in straight rows within the circular tube sheet, will be divided into four tube groups or quadrants and four mobile test units or carts will be employed, one for each of the quadrants. Each mobile test unit is in air supply, electrical and electronic communication with the control unit via the umbilical of each individual mobile test unit. Tube locations will be identified by quadrant and by row within the respective quadrants. The control unit will receive signals representing test results for reactor tubes and will electronically compile a single reactor service report that will indicate the resulting pressure test of each of the reactor tubes.

At times some of the reactor tube positions will be rendered inactive, such as when a faulty reactor tube has been plugged or when a reactor tube position is used for mounting a thermocouple or other temperature or pressure measurement sensor. When inactive tube positions are encountered, the worker will loosen the probe position adjustment wing-nut 96 for that particular test probe and move it upwardly to an inactive or non-test position as shown in FIG. 9. When a test probe is raised from its active position on the test probe manifold a magnetic type limit switch, mechanically actuated limit switch, or any other suitable condition signaling device, will change to a non-test mode. This will cause a non-test signal to be transmitted electronically from the mobile test unit that is involved to the computer of the control unit via an appropriate conductor of the umbilical 38. This non-test signal will be recorded in electronic memory for that particular tube position and will be indicated in the electronic record or in any print-out that is generated to show the test results for the catalytic reactor.

Since the control units may not be capable of positioning the array of test probes in registry with certain reactor tube openings, depending on the location of the reactor tubes relative to the internal wall surface of the reactor shell, it is desirable to provide operating personnel of the mobile test units or carts with a manual capability for testing hard to reach tubes. Yet it is also desirable that all reactor tube tests, whether mechanized or manually conducted, provide electronic test signals that are specifically related to the particular reactor tubes that are manually tested and are communicated to the electronics of the control unit and incorporated within the overall test results for the reactor. Accordingly, each mobile test unit is provided with a manually positioned test wand as shown generally at 134 in FIG. 8. Essentially, the manually positioned test wand 134 has virtually all of the features shown in FIGS. 5, 6 and 7, except that it is normally supported on the mobile test unit in a "home position" and is manually retrieved from the mobile test unit and is independently used to conduct D-P testing of reactor tubes that cannot otherwise be readily accessed by the test probe array of the mobile test unit. The test wand 134 has a seal actuating mechanism shown generally at 136 which may be substantially identical to the toggle linkage energized seal actuating mechanism of FIGS. 6 and 7. The test wand 134 also has an elongate tubular member 106 that functions as an air supply to a reactor tube during DP testing. A tee member 96 is mounted to the elongate tubular member 106 and provides for connection of an air supply tube to the tee member via an elbow fitting 101 and a coupler/orifice member 102 that functions as a supply tube connector and also functions to establish the test pressure and test air volume for conducting back-pressure tests. The tee 96 also provides for connection of a pneumatic back-pressure line 100 through which the back-pressure of a reactor tube is conducted to a pressure sensor within the mobile test unit which measures the pneumatic pressure that is present within the elongate tubular member 106, which is reactor tube back-pressure.

Since the D-P testing system of the present invention will be moved from one reactor to another from time to time or may be shipped to another location, it is appropriate that the mobile test units and the control unit be easily and quickly disassembled and packaged for handling and shipment. For this purpose the mounting plate 62 is secured to the cart housing by several, typically 4 threaded stud and nut assemblies 63. As mentioned above, the test probe manifold, including its plurality of test probes and its cylinder motors 74 are fixed to the mounting plate. Thus, by removing only 4 nuts from the threaded studs, the mounting plate and all of its testing manifold assembly is removed as a unit. This unit can then be separately packaged so that it will not become damaged or lose its adjustment settings during handling and shipment. The pneumatic supply line 98 and the back-pressure line 100 of each D-P test probe, including the test probe of the manually positioned test wand 134 all extend to the mobile test unit housing and are connected to removable air supply and return connector modules 139 and 141 which are shown in FIG. 4. The connector modules, as shown in FIG. 6, are received by respective connector module mounting base members, one being shown at 137, which are fixed to the housing structure 44 of the mobile test unit. The connector modules each incorporate a plurality of mounting and sealing projections that engage within like mounting and sealing receptacles of the mounting base members and are retained in assembly with the respective mounting bases 137 by bolts or screws. This feature enables simple and efficient connection and disconnection of all of the pneumatic supply and back-pressure or return lines in unitary fashion. Though only one removable connector module is shown in FIG. 6, typically two connector modules will be used, as shown at 139 and 141 of FIGS. 2 and 4, to provide for connection and disconnection of the 18 pneumatic supply and back-pressure lines and the pneumatic lines that are employed for cylinder motor operation.

The test wand 134 incorporates a support tube 140 to which is mounted a handle element 142 to enable the test wand to be easily handled by a worker. The support tube 140 is adapted to receive a wand support pin 144 which, as shown in FIG. 10, is mounted to a support bracket 146 that is fixed to the structure of the mobile test unit. The wand support bracket is shown to be mounted to one of the cylinder support brackets 64, such as by welding, bolting or the like or it may be mounted directly to the mounting plate 62 if desired. Thus, in preparation for transporting the DP testing system, when the mounting plate 62 is removed from the flat wall section or panel 60 of the mobile test unit housing 44, the wand support bracket and its connected electrical components will remain connected to the mounting plate. This feature, as mentioned above, permits simple and efficient assembly and disassembly of the mobile test unit 32 so that the various components there will not be subject to damage during shipment and handling. The wand support pin 144 is provided with a tapered or conical upper end 148 that serves as a guide surface for guiding the support tube 140 of the test wand to its supported relation with the wand support pin 144. The substantially horizontal flange 150 of the wand support bracket 146 defines wand positioning recesses 152 and 154 that are arranged in angularly offset relation with each other, such as 90° offset relation for example. The wand positioning recesses 152 and 154 are each adapted to receive a portion of the tubular member 106 or other suitable wand positioning structure of the test wand 134 and establish two angularly offset orienting positions for the test wand.

A pair of wand position contact brackets 156 and 158 are mounted to the wand support bracket 146, such as by welding and provide respective mounting flanges 162 and 164 to which are mounted a pair of adjustable magnetic limit switch members 166 and 168 having magnetically actuated limit switch elements and electrical limit switch circuit conductors located therein. The limit switches are protected by cover members 170 and 172 which may simply take the form of polymer potting material that provides an external closure for the limit switches of switch and conductor cavities within the adjustable magnetic limit switch members 166 and 168. Electrical conductors, one being shown at 174, are connected to the respective adjustable contact members 166 and 168. When the test wand is properly positioned for support and orientation at its "home position" by engagement of a wand positioning member within the wand positioning recess 152 the mounting bracket 146 and the wand support pin 144, an adjustable magnetic switch actuator 176, supported by a mounting flange 178 of the tubular member 140 of the test wand 134, will be in actuating proximity with one of the magnetic limit switch elements 166 and 168, thus confirming electronically the condition of the test wand. One wand orienting position, the "home position" is established when the wand positioning structure of the wand orients the wand to a position positioning the magnetic switch actuator 176 in actuating registry with the magnetic switch 166. The other wand orientating position, the "reset position" is established when the wand positioning recess 154 of the flange 150 is engaged by the wand positioning structure and the magnetic switch actuator 176 is positioned in actuating registry with the magnetic switch 168. When the magnetic switch 168 is actuated an electronic signal is transmitted via the switch conductors to indicate that the testing wand has completed a testing operation and is ready for conducting differential pressure testing of the next reactor tube in the testing sequence. Thus, the magnetic switches 166 and 168 permit the computer of the control unit to correlate the tube numbering sequence with the differential pressure tests that are being conducted by using the manually positioned testing wand 134.

Alternatively or additionally, the test wand 134 may be provided with a manually operated reset switch 169 that is mounted to the wand near the wand handle 171 that is grasped by testing personnel to conduct D-P tests. The reset switch 169 obviates the need for testing personnel to position the test wand on the wand support pin to cause a reset signal after each reactor tube test has been completed. The operating personnel, in the event the manually positioned and actuated testing wand is employed, will only need to ensure that the reset switch 169 is actuated after completion of a test before testing the next reactor tube in numerical sequence and to ensure that the reset switch is manually actuated only once between tests. Otherwise, the numerical reactor tube counting system or the differential pressure testing system could lose its correlation with the numerical sequence of the reactor tubes of the catalytic reactor being tested.

Referring again to FIGS. 2 and 3, during DP testing procedures a service worker will grasp manipulation handles 180 and 182 that are fixed by bolts or by any other suitable means to the frame structure of the mobile test unit and will apply appropriate forces to move the mobile test unit to desired locations on the upper tube sheet of the reactor. The worker will first orient the mobile test unit in linear registry with a selected row of reactor tubes and will confirm registry of the test probe array of the mobile test unit with an initial group of reactor tubes of that row, confirming correspondence at that time of the initial reactor tube identification with the reactor tube identification sequence that is indicated by the mobile test unit and control unit electronics. After testing of the initial group of reactor tubes of any given row, the worker will simply roll the mobile test unit linearly along the selected row of reactor tubes of upper tube sheet to sequentially align the array of test probes with the next group of reactor tube openings. This will continue until each of the reactor tubes of that particular row have been successfully tested. During the reactor tube testing process each of the reactor tubes is individually tested and signals representing the test results of each reactor tube will be conducted to the system electronics and will be processed and recorded. Also, the computer program of the system electronics can identify tubes within a predetermined satisfactory test range in a particular color, green for example, and can identify reactor tubes that test above the predetermined satisfactory test range in a different color, red for example, and will identify identify reactor tubes that test above the predetermined satisfactory test range in a yet different color, yellow for example. This will enable a computer print-out to be done which will permit the reactor test personnel or the reactor owner to easily identify the test results for any reactor tube that has tested out of range. The computer print-out will provide the reactor owner with test documentation enabling the decision making capability for cleaning, re-filling and re-testing any reactor tube that has been identified as having exhibited excess differential pressure or insufficient differential pressure as the result of its testing. The color coded print-out will also allow personnel to easily visualize the accuracy of the catalyst loading process so that the process output of the reactor can be easily determined before the reactor is placed back in service. Any remedial action that is needed to ensure the optimum process output of the reactor can be immediately done, thus minimizing the down time of the reactor.

The service worker will also be involved in operating the mobile test unit for D-P tests and thus must be able to visualize the status of the test procedure that is in progress. During testing activity, especially since the worker will be using the mobile test unit in the confined space within a reactor shell, the worker will often need to change positions relative to the mobile test unit. To permit a worker to visually inspect the status of a testing procedure regardless of the worker's position relative to the mobile test unit, as shown in FIGS. 2 and 3 an inspection pedestal 184 is pivotally mounted to the upper portion of the mobile test unit housing 40 and has an inspection panel 186 on which are mounted a plurality of cart position signal indicators 185 that are sequentially illuminated responsive to a wheel actuated measurement encoder system shown in FIG. 5 to indicate linear movement of the mobile test unit to a position registering its test probe array with the next group of reactor tubes to be tested. One of the position signal indicators 185 is illuminated or otherwise actuated when the mobile test unit has moved one tube position past the next succeeding group of reactor tube positions, thus indicating to the worker that the mobile test unit has moved too far and must be moved back to the proper position for alignment of its test probe array with the next succeeding group of reactor tubes. Preferably, the signal indicators 185 take the form of lights, such as LED's; however it should be borne in mind that audible signal devices may be employed to alert the worker and thus ensure that the test probe array is in registry with the proper group of reactor tubes according to the tube identification sequence of the catalytic reactor. The signal indicators may be inspected by testing or supervisory personnel any time during the testing process to confirm proper positioning of the mobile test unit with respect to according to the tube identification sequence of the catalytic reactor. With reference to FIG. 5, one of the wheels 187 of the mobile test unit 32 is provided with an encoder 189 that is rotationally driven by the axle 191 corresponding to wheel movement. Encoder movement is sensed by a sensor 193 and is transmitted to the position indicating circuit of the system computer via signal conductors 195.

The inspection pedestal 184 may be rotated to any desired position by the testing personnel to ensure that the signal indicators can be easily visualized at any point during the testing process. The inspection pedestal 184 is of essentially hollow construction and serves as a housing in which components of the system electronics of the testing system are located. The rotatable support for the inspection pedestal is constructed to maintain the integrity of electronic signals of the various signal indicators during rotary positioning movement thereof.

As evidenced particularly by FIG. 3, for purposes of electrical power, pneumatic pressure and signal transmission, the umbilical 38 will be provided with a first conductor 188 for pressurized pneumatic fluid and electrical power and incorporates a flexible pneumatic tube about which is located a plurality of electrical power conductors, all covered by a protective sheath. A second conductor 190 is provided for network connection between the mobile test unit 32 and the control unit 34 and incorporates a bundle of electrical conductors. A third conductor 192 is known as an encoder conductor which is employed for computer network communications, particularly for transmitting DP test data from the mobile test units to the computer of the control unit. These conductors are each provided in quick-disconnect or plug-in form so that the conductors may be removed from the testing system and stored or safely packaged when the test system is being prepared for handling and transit to another location.

Referring now to FIGS. 11 and 12, the control unit 34 comprises a control unit housing 200 which is suitably mounted on wheel assemblies 202 to permit the control unit to be mobile so that it may be positioned as desired in relation with the reactor structure. Unlike the mobile test units, which are somewhat restricted to linear movement on the wheel assemblies thereof, some or all of the wheels of the control unit may be in the form of casters. However, when the control unit has been positioned as desired it will typically remain in this position until the reactor servicing procedure has been completed. Thus one or more of the wheel assemblies 202 may be capable of being locked to minimize the possibility of undesirable movement of the control unit. As mentioned above, during reactor tube D-P testing the control unit is typically located externally of the reactor shell or at least off to the side of the upper tube sheet of the reactor. Typically, once the control unit is desirably located, it will not be moved during D-P testing of the reactor tubes. Only the mobile test units 32 need to be selectively moveable for alignment of the various test probes with the reactor tubes. The control unit housing 200 has a front wall 204 having an upper portion defining a display panel 206 and has a panel cover 208 that is connected to the front wall 204 by a piano hinge 210. When the control unit is being used, the panel cover 208 is normally rotated to a position where it rests on a top wall 212 of the control unit housing. For handling and shipment, the panel cover is rotated to its closed position about the piano hinge and is secured at its close position by one or more closure cover lock devices 214. In its close position the panel cover is positioned in front of the display panel 206 and thus protects the display panel and each of its components from being contacted during handling and shipment of the control unit.

A touch-screen type color monitor 216 is mounted within the control unit 34 with its viewing screen being located in the display panel 206. A high performance computer 218 having an Ethernet interface is also mounted within the control unit and receives D-P test data from each of the control units during DP testing of the reactor tubes of a catalytic reactor. The computer and its keyboard are electronically coupled with the color monitor 216 and with a color printer 220 that is mounted on a retractable printer support tray 222 that permits the printer to be supported in stored condition within the control unit when the printer is not in use and is extendable from the control unit housing 200 to enable operation of the printer. The retractable printer support tray 222 is provided with a closure panel 224 so that in the retracted position of the printer support tray the closure panel functions as a closure for the printer access opening 226 of the housing side wall 228. A retractable keyboard tray 230 is also mounted within the control unit housing 200 and provides support for a keyboard that is electronically coupled with the computer 218. Preferably, the keyboard is built into the retractable keyboard tray or in the alternative a standard computer keyboard may simply be mounted to or supported by the retractable keyboard tray. The tray 230 is provided with an actuating handle 232 thus enabling the keyboard tray to be extended for use or retracted for storage.

The control unit housing is provided with housing recesses within which electrical, Ethernet and pneumatic connectors are located. If desired, the recesses may be provided with protective closures that are assembled to the control unit housing or if connected by hinges, are closed and locked to protect the various connectors from damage during handling and shipment of the control unit. A plurality of quick-disconnect modules, one of which is shown at 234 in FIG. 11 are mounted to the side wall 228 of the control housing within a housing recess 236 (typically 4 quick-disconnect modules are employed) and provide for connection of umbilical members 38 of the mobile test units thereto. Thus electrical power, Ethernet connection, signal transmission and pneumatic supply are all furnished to the mobile test units via the control unit system. Electrical power supply for the control unit and thus the mobile test units as well is furnished via a power connector 238 that may be plugged into a receptacle of any suitable source of electrical power. The control unit 34 may generate compressed air for testing and blow-down if desired; however, since a high volume of compressed air is typically employed for reactor tube blow-down, it is deemed preferable to provide the control unit with a remote source pneumatic connection 240 to which an air supply hose 242 can be connected. Within a housing recess at the lower portion of the side panel 244 of the control unit housing 200 is located a power control system shown generally at 246 which includes an on-off switch 248. The pneumatic circuitry within the control unit also includes a pressure regulating capability to ensure that the air supply pressure and volume are optimum for testing and blow-down processes according to the number of testing carts that are being used at any given time.

The relationship of the control unit 34 with a plurality of mobile test units 32 is shown schematically in FIG. 12. The control unit 34 typically compressed air from a suitable source A/S, such as compressed air piping that is typically present in refineries, chemical facilities and petrochemical facilities. However, if desired, a mobile air compressor may be provided at the site of the reactor being serviced. In some cases the control unit itself may be provided with the capability for generating a compressed air supply. The control unit 34 is provided with compressed air handling conduit system having a filter F and a regulator R, with the conduit system terminating at a plurality of pneumatic connectors 35 that are typically quick disconnect connectors to which the compressed air supply conduit of each of the umbilical members 38a, 38b, 38c and 38d is capable of being releasably connected. As mentioned above, the umbilical members 38a–38d each include a power conductor for supplying electrical power to each of the mobile test units and includes an Ethernet interface conductor or cable providing for electronic signal transmission between the mobile test units and the on-board computer of the control unit.

With reference to FIGS. 13 and 14, each mobile test mobile test assembly may be designed to accomplish lateral shifting of the position of the array of spaced test probes relative to the mobile test unit structure to enable a greater number of reactor tubes to be engaged by the test probe array and to gain access to reactor tube openings that are located close to the reactor shell. A linearly moveable test probe mount shown generally at 250 and constituting a slide bearing assembly is connected by bolts, screws or by any other suitable means to the mounting plate 62 of the mobile test unit housing 44 and provides for support and mobility of a guide bar 252 of rectangular cross-sectional configuration. Normally, the test probe mount 250 will be locked against linear movement by a suitable lock or retainer mechanism such as a spring urged locking pin 254 that in its locked position engages within a lock receptacle 256. When linear movement of the test probe array is intended, the worker will simply move the spring loaded locking pin 254, thus releasing it from the lock receptacle 256 and permitting manual lateral movement of the test probe array to a desired position in registry with a group of reactor tubes. After the testing procedure for these reactor tubes has been completed, the array of test probes is returned to its locked or retained position at which point the spring urged locking pin 254 will again be positioned in locking engagement within the lock receptacle 256.

With reference to FIGS. 14–16 the linearly moveable test probe mount 250 incorporates one or more bearing bar members 258 and 260 that are fixed to the mounting plate 62 and are positioned in aligned registry. Moveable bearing blocks 262 and 264 each define bearing receptacles within which the fixed bearing bars are received. The rectangular guide bar 252 is mounted to the bearing blocks 262 and 264 and is thus laterally moveable along with the bearing blocks. Though the bearing blocks and bearing bars may be of any suitable length, it is desirable that their length permit effective controlled lateral movement of the guide bar 252 in the range of 6 to 12 inches or more.

A plurality of test probe assemblies 266, shown in FIG. 15, are disposed in adjustable and supported relation with the rectangular guide bar 252. The test probe assemblies 266 incorporate all of the features of the test probe assemblies 90 of FIG. 6 but have slightly different construction and function. Similar features are designated by like reference numerals. A guide block 268 defines a horizontally oriented rectangular slot or passage 270 within which the elongate rectangular guide bar 262 is moveably received. The horizontally oriented rectangular slot or passage 270 defines a slot opening 272 within which one or more guide bar mounting members 273 are moveable. The guide bar mounting members mount the guide bar in immoveable relation with the bearing blocks 262 and 264. A first locking wing nut or bolt 274 is mounted to the guide block 268 and is tightened to secure the guide block in immoveable relation with respect to the guide bar 252. This first wing nut or bolt is loosened to allow the guide block to be selectively positioned on the guide bar, thereby permitting pitch adjustment of the array of test probes to be easily accomplished to adapt the D-P testing system to the pitch of the reactor tubes being tested. The guide block 268 also defines a vertically oriented passage 276 of circular cross-sectional configuration within which the substantially rigid tubular member 106 is moveably received. A second locking wing nut or bolt 278 is mounted to the guide block 268 is mounted to the guide block 268 and is tightened to secure the tubular member 106 in immoveable relation with respect to the guide block. In the event one of the test probes needs to be retracted to a non-test position, such as when a thermocouple or plug is encountered at a tube position, the wing nut or thumb screw 278 is loosened to permit manual raising of the guide block. The guide block is secured at this raised position simply by tightening the wing nut or thumb screw 278 and is returned to the test position thereof by loosening the thumb screw, moving the test block and then again tightening the thumb screw.

With reference to FIG. 18 and as mentioned above, it is desirable to achieve independent and individual testing of each or the reactor tubes of a tube and shell type catalytic reactor and to provide a test report that identifies the measured back-pressure of each tube. It is also desirable to achieve accurate test results for each reactor tube with minimal testing time for each filled reactor tube to thereby provide for efficiency of the testing procedure. To ensure the accuracy of the testing procedure it is also desirable to provide for calibration of the testing system without interfering with the condition of the testing probes of the mobile test units. Accordingly, each of the mobile test units is provide with a pneumatic control valve system shown generally at 280 that is capable of delivering to the catalyst filled reactor tubes compressed air at the desired pressure and volume for accomplishing blow-down and testing of each reactor tube. The pneumatic control valve system 280 for each of the mobile test units incorporates an air supply body or block 282 having internal air-supply passages defining air circuits and manifolds for supply of compressed air at blow-down pressure and volume and compressed air to be used for differential pressure testing of the reactor tubes. Air circuit passages in connection with the respective manifold passages terminate at an upper surface 284 of the air supply body or block 282. Compressed air for blow-down and differential pressure testing is supplied to the air supply body or block 282 by any suitable air supply A/S, such as an air compressor or a pneumatic supply line of the plant or facility within which the reactor is located. The compressed air is supplied to the air supply body or block 282 via an air supply system incorporating a filter F and a pressure regulator R. On the "Blow-down" side of the pneumatic control valve system 280 the plurality of shuttle valve outlets are in communication with the respective blow-down pressure supply lines 100, shown in FIG. 6. Likewise, the plurality of shuttle valve test pressure supply outlets are each in communication with a respective one of the test pressure supply lines 98, also shown in FIG. 6.

The pneumatic control valve system 280 plurality of test/blow-down valve members 286 are mounted to the upper surface 284 of the air supply body or block 282 and in sealed relation with the air circuit passages, such a by means of bolts or screws 288. The valve system 280 shown in FIG. 18 is provided for a blow-down and differential pressure testing system having 8 test probes and a manually positioned and operated test wand such as is shown in FIG. 9. Another of the 10 valves that are shown is provided for purposes of calibration, so that calibration of test pressure may be accomplished with disturbing the test probe and test wand systems. The valve members 286 are preferably in the form of solenoid actuated shuttle valves having an off position, a position for blow-down and a position for differential pressure testing. These positions of the valve members are controlled by the blow-down and test systems of each of the mobile test units by selective control of the mobile test unit system by the operating personnel.

For purposes of simplicity and understanding, a single blow-down and testing circuit for a single testing probe is shown schematically in FIG. 18. Each solenoid actuated shuttle valve 286 is provided with a blow-down circuit connector 290 to which an inlet end of a blow-down conduit 292 is connected. The outlet end of the blow-down conduit 292 is in communication with the back-pressure sensor conduit 100 which is in turn connected with the tee fitting 96 of the testing probe 90. The pressure sensor conduit 100 is in communication with a pressure sensor element 294 which measures the back-pressure of a reactor tube and transmits a back-pressure measurement signal to the computer of the control unit 32 via an electron signal conductor 296 of the respective umbilical member. The valve system permits the mobile test units to provide for operation of each mobile test unit in a test mode, and blow-down and test mode or a blow-down mode, depending upon the condition of the valve system as set by operating personnel.

When the D-P testing units are being used within a catalytic reactor, reactor structural elements located adjacent some reactor tube openings may make it difficult to access certain groups of reactor tubes for testing when the test probe array is assembled in fixed relation with a test unit housing. Though these reactor tubes may be accessed by the manually positioned and actuated testing wand, the use of the testing wand for conducting D-P tests of a large number of reactor tubes may detract from the commercial viability of the reactor tube testing system. To overcome this potential disadvantage, as set forth in FIG. 19, according to an alternative embodiment of the present invention, the mobile test units 32a–32d, being identified at 32 in FIGS. 2 and 3, is provide with a pneumatic extension interface, shown generally at 300, having a plurality of pneumatic tubes 302, the same number of pneumatic tubes that extend from the housing of the mobile test unit to the test probes and pneumatic actuators, and having plug-in type connector module members 304 and 306. The connector module members are capable of being placed in releasable assembly with the connector modules which may be interconnected with pneumatic connector modules 139 and 141 such as by means of module connector screws 308. The pneumatic tubes 302 of the pneumatic extension interface 300 may be of any length that is suitable to achieve positioning of the test probe array in desired remotely located relation with the mobile testing unit 34 so as to engage the test probes thereof within a plurality of reactor tube openings. For purposes of simplicity the pneumatic tubes 302 are shown to be straight and loosely assembled; however it is preferable that the pneumatic tubes, which are typically flexible polymer tubes, be secured in one or more bundles by plastic ties or other suitable retainer devices. It is also to be understood that each of the test probes, the test wand and the linear actuators of the test probe array are each provided with an air supply tube and an air return or pressure signal tube. At its opposite or terminal end the pneumatic extension interface 300 is provided with a connector module element 310 to which each of the pneumatic tubes 302 are connected. The connector module element 310 provides a plurality of receptacles each being adapted to receive one of a plurality of connector projections of the connector module member 136. The module assembly screws or bolts 138 will be employed to secure the connector module members 310 and 136 is sealed releasable assembly. With the pneumatic extension interface 300 in assembly between the mobile test unit 34 and the connector module member 136, operating personnel can simply and efficiently disassemble the test probe array from the mobile test unit and manually position its plurality of test probes in blow-down and testing relation with a plurality of reactor tubes.

System Architecture Overview

A summary of the features of the DP testing system of the present invention is as follows:

Control Unit A single control unit is typically located externally of a reactor shell and consists of a control unit housing containing a high performance computer with an Ethernet interface and having a touch-screen color monitor and a color printer. The control unit has a network hub, TVSS (transient voltage), UPS (battery backup), and centralized utility connections (electrical power, computer network and pneumatic supply).

Test units At least one and preferably a plurality (generally 4) mobile test units are positioned within a reactor shell and on the upper tube sheet during a DP testing procedure. Each of the mobile test units comprises a test unit housing having PLC I/O rack and associated hardware, operator interface (two line message display), cart configuration (8 channel or 1 channel) indicating pilot lights, test mode (blow-down and/or test) indication pilot lights, linear positioning system indicating pilot lights, eight channel manifold (having the capability for disabling individual channels due to the presence of plugs, thermocouples, etc. at tube positions). The mobile test units incorporate a single channel manually positioned wand (for testing tubes at the end of a row and/or tubes that are located too close to the reactor wall). The mobile test units are connected to the control unit by umbilical assemblies which supply the required utilities (electrical power, air and network).

Reactor Tube Addressing Convention

The reactor tube addressing convention incorporated within the DP testing system of the present invention assigns a unique tube address to each reactor tube, by Row Number and Tube Number (i.e., Row 10/Tube No. 25=010.0025). The reactor configuration (i.e., number of rows and number of tubes per row) must be entered prior to commencement of testing. Note: Row No. 1/Tube No. 1 is the uppermost and leftmost tube. Reactor testing always progresses from left-to-right and from top-to-bottom.

Machine Feature Overview

DPT Testing Features

Sequential testing Sequential testing of 8 reactor tubes (assuming a manifold having 8 test probes; a manifold having more or less test probes may be employed as well), following entry/confirmation of row number and tube number of the first tube of a group being engaged by the 8 tube array of test probes of a mobile test unit or single channel testing of one reactor tube, following entry/confirmation of row number and tube number. Note: each of the mobile test units accomplish auto-configuration to 8 channel or 1 channel based on the state of manifold and wand limit switches.

Channel disablization The DP testing system has the capability for disabling individual channels of the 8 channel manifold and the single wand channel when tube positions are disabled, such as when tubes are plugged or when thermocouples or other measuring devices are located at a tube position. All disabled reactor tubes are logged and can be reported.

Test Modes

Blow-down only, Blow-down and test or Test only. Note: Blow-down bypasses the channel orifice to provide full air pressure blow-down.

Normal sequence testing (channels 1 through 8). This is the normal testing sequence where reactor tubes are sequentially tested in accordance with their numerical order. In this case the reactor tubes are readily accessed by the test probe array of the particular mobile test unit that is involved.

Inverted sequence testing An inverted sequence test (channels 8 through 1) is selected when reactor tubes are located so as to be inaccessible by the test probe manifold due to cart orientation. Note: inverted sequence testing is typically required at the top of the reactor where a mobile test unit needs to be rotated 180° to permit test probe access to certain reactor tubes because of their location near the wall of the reactor.

Test Number A test number field is provided to permit separation of data into different tests on different zones and/or loads.

Cross-checking of the number of reactor tubes tested vs. the number of reactor tubes configured. Cross-checking is accomplished at the beginning of a test sequence, as well at the end of a test sequence. The mobile test unit worker is alerted when errors occur, and is referred to the control unit worker for resolution. If the error cannot be resolved, as with a reactor configuration error, a total row re-test is required. Three conditions can cause tube count errors, which are (1) tubes missed (2) tubes duplicated and (3) reactor configuration error.

Linear Positioning System A linear positioning system of each mobile test unit provides visual indication as to the progress of the mobile test unit index to the next set of 8 tubes to be tested. The "tube pitch", in inches, is entered during reactor configuration data entry and is required to permit the linear positioning system to properly calculate the correct index distance. The system detects an "index complete" through the cycling of the manifold or wand limit switches, and resets the linear positioning system for the next index.

Calibration Checking of Delta P Transmitter Each mobile test unit will automatically initiate a calibration check, every 96 channels, which will check the delta P transmitter calibration against a fixed 20 psi reference pressure.

High and Low Air Supply Pressure Each mobile test unit incorporates an air supply pressure monitoring system and accomplishes provides a signal to alert the mobile test unit worker when the air supply pressure is out of the predetermined range. This signal may be in the form of a light signal or audible signal or both.

Counting System Each mobile test unit is equipped with three counters which are used to monitor testing activities. These counters include:

Calibration Counter The calibration counter will trigger an auto-calibrate check sequence after every 96 channels.

Cumulative Counter The cumulative counter is a free running, resetable counter which is intended to be used to compare testing progress between respective mobile test units.

Accounting Counter The accounting counter is a free running, non-resetable counter which auto-resets at 30,000 (intended to be used to track the total number of tests that are performed by each of the mobile test units). This counting data is intended to be used for purposes of accounting.

Data Analysis Features

All delta P data is logged to a Microsoft Access database for graphical analysis and reporting, grouped by project number and test number.

An operator interface screen provides a graphical representation of the reactor configuration variables: Number of rows and number of tubes per row (for example a solid black square on the operator interface screen identifies a tube that is not configured and an open square identifies a tube that is configured, but not tested. Note: Tube number 1 is always displayed in the uppermost-leftmost corner.

The operator interface screen identifies operator input and manipulation of the DP target (psi), and independent tolerances, high and low, permits "What if" scenario analysis, (i.e., What-if the tolerance (high) is 5.1% instead of 5.0%).

DP test results and the associated DP target and tolerance assumptions are graphically displayed on the "Data Analysis Detail" screen, which provides a color representation of the test results: (i.e., the color green represents "OK", blue represents "Out of Spec (OOS) Low", red represents "Out of Spec High, yellow represents "Channel Disabled" and cyan represents "Row Re-test Required".

The final results of a reactor tube testing procedure can be documented by printing the "Data Analysis Detail" screen or screens with an on-board printer of the control unit and/or by providing Microsoft Access database reports. These reports include (1) a Delta P "Out of Spec" Query report (2) a Delta P "Calibration" Query report, (3) a Delta P "Disabled" Query report and (4) a Delta P "Comprehensive" Query report.

The Delta P analysis features include the capability to analyze the current project, as well as historical projects that are stored on ZIP250 disks.

Data Entry Overview (Performed by Control unit Operator)

Data Collection—Data Entry Requirements

The following data entry is required from the associated operator interface screen, shown in parenthesis:

Project Data Entry (Project Overview Screen) The Project Overview Screen will identify (1) the project number, (i.e., "yy###,", (2) customer name, (3) customer location and (4) reactor number and (5) the current test number, which is used to separate the test data by zones and/or loads.

Reactor Configuration Entry (Reactor Configuration Screen) The Reactor Configuration Screen will show the number of rows and the number of tubes per row. This data is used to cross check the number of tubes tested in each row, and to alert the operator to errors (i.e., "tubes missed", "tubes duplicated", and/or "reactor configuration error"). The reactor configuration screen will also display "Tube Pitch (inches)", which is used by the linear positioning system to provide a visual indication via pilot lights, for proper indexing of the mobile test unit to the next set of 8 reactor tubes.

Mobile Test Unit Set-up (Cart 1 through 4 screens, assuming four mobile test units are employed) The "Test Mode Set-up" will be established to indicate the (1) "Blow-down Mode Enable/Disable" selection (2) the Blow-down Pressure Set-point (psi) and (3) the "Duration Set-point (seconds)".

Mobile Test Unit Configuration Selection The cart operator will select "Normal Sequence", which sets the testing sequence for channels 1 through 8 or the operator will select "Inverted Sequence" which sets the testing sequence of the mobile test unit for channels 8 through 1. As mentioned above, the selection of "Inverted Sequence" is typically required for testing one or more rows of reactor tubes at the top of the reactor.

Data Analysis—Data Entry Requirements

The following data entry is required from the associated operator interface screen, shown in parenthesis:

Data Analysis—Project Selection (Project Overview Screen or Data Analysis Detail Screen)

The "Current Project" and "Historical Project (requires entry of a pre-defined system password).

Data Analysis—Data Entry (Project Overview Screen or Data Analysis Detail Screen)

The current project is displayed, including "Test Number", "DP Target (psi)", "Tolerance (High)", and "Tolerance (Low)". A "Historical Project" is also displayed, including project number and test number.

Operator Interface Screen Summary

The operator interface screen summary provides a display of (1) Project Overview (2) Reactor Configuration (3) Cart number (carts 1 through 4) and (4) Data Analysis Detail.

In view of the foregoing it is evident that the present invention is one well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive, the scope of the invention being indicated by the claims rather than the foregoing description, and all changes which come within the meaning and range of equivalence of the claims are therefore intended to be embraced therein.

I claim:

1. A method for conducting blow-down and differential pressure testing of the catalyst tubes of a tube and shell type catalytic reactor having an upper tube sheet and a multiplicity of reactor tubes each having the upper ends thereof extending downwardly from the upper tube sheet, comprising:

providing at least one test probe defining a testing path having an air supply thereto and a restricted orifice therein and having a selectively activated blow-down path in communication with the air supply and bypassing the restricted orifice;

establishing sealing of the test probe with a selected reactor tube;

activating the blow-down path and injecting compressed air from the air supply into at least one reactor tube at a predetermined pressure and volume for reactor tube blow-down;

de-activating the blow-down path and controllably injecting a pressurized gas through the orifice and into a reactor tube at a predetermined test pressure and volume determined by air supply pressure and by the restricted orifice;

measuring the back-pressure of the reactor tube and developing an electronic signal representing the measured back-pressure; and recording the electronic signal representing the back-pressure measurement.

2. The method of claim 1, wherein an air injection passage is defined by said at least one test probe through which compressed air is injected into a reactor tube and a blow-down passage bypasses said restricted orifice and communicates said air supply with said air injection passage and a test/blow-down valve controls the flow of compressed air within said air injection passage and said blow-down passage, said method comprising:

said step of activating the blow-down path being actuating said test/blow-down valve to a blow-down position thereof causing compressed air from said air supply to by-pass the restricted orifice and flow directly into said air injection passage and thence into a reactor tube; and said step of de-activating the blow-down path being actuating said test/blow-down valve to a test position and directing flow of compressed air from said air supply through said restricted orifice and into said air injection passage and thence into a reactor tube.

3. The method of claim 1, wherein said at least one test probe being a linearly arranged test probe array having a plurality of test probes mounted to a mobile test unit and being moveable relative to the mobile test unit between a testing position for sealing engagement with a plurality of reactor tubes and a non-testing position being retracted to non-sealing positions with respect to the reactor tubes and having a test probe actuator being selectively energized for moving said test probe array to said testing and non-testing positions relative to the mobile test unit, said method comprising:

positioning said mobile test unit with said plurality of test probes of said test probe array in registry with a like number of linearly arranged reactor tubes;

actuating said test probe actuator to a test position and causing movement of said plurality of test probes of said test probe array to said testing position and in testing engagement with the like number of reactor tubes;

conducting differential pressure testing of the reactor tubes; and actuating said test probe actuator to said non-test position and causing retraction movement of said plurality of test probes of said test probe array from the reactor tubes.

4. The method of claim 2, wherein said test probe array is mounted to said mobile test unit for lateral movement relative thereto, said method comprising:

moving said test probe array laterally relative to said mobile test unit and aligning at least one of the test probes thereof with at least one of the reactor tubes.

5. The method of claim 1, wherein said at least one test probe being a linearly arranged test probe array having a plurality of test probes mounted to a mobile test unit and being moveable relative to the mobile test unit between a testing position for sealing engagement with a plurality of reactor tubes and a non-testing position being retracted to non-sealing positions with respect to the reactor tubes and having a test probe actuator being selectively energized for moving said test probe array to said testing and non-testing positions relative to the mobile test unit, said method comprising:

removing said linearly arranged test probe array from said mobile test unit;

manually positioning said linearly arranged test probe array with said plurality of test probes in testing engagement with a like number of reactor tubes; and conducting blow-down and differential pressure testing of the reactor tubes.

6. The method of claim 5, wherein pneumatic tube connector modules interconnect each of said plurality of test probes with said mobile test unit, said method comprising:

assembling a pneumatic extension interface in assembly with each of said connector modules and permitting blow-down and differential pressure testing with said moveable test probe array at locations within the catalytic reactor and remote from said mobile test unit.

7. The method of claim 1, wherein wheels are mounted to the mobile test unit and a linear encoder is driven by at least one of the wheels and has electronic circuitry selectively activating test unit position signal devices responsive to selective linear movement of the mobile test unit, said method comprising:

moving the mobile test unit linearly a distance causing activation of said position signal devices indicating movement of the mobile test unit from a previous testing position to a consecutive testing position.

8. The method of claim 7, wherein a plurality of linear encoder actuated position indicator signal devices are mounted to the mobile test unit and wherein said step of moving the mobile test unit comprises:

moving the mobile test unit linearly a distance causing energization of a first position indicator signal device indicating movement of the mobile test unit from a previous testing position toward the next consecutive testing position;

continuing linear movement of the mobile test unit until a second of the position indicator devices becomes energized indicating movement of the mobile test unit to a location near the next consecutive testing position;

further continuing linear movement of the mobile test unit until a third of the position indicator devices becomes energized indicating location of the mobile test unit at the next consecutive testing position; and in the event of energization of a fourth of the position indicating devices, indicating linear movement of the mobile test unit past the next consecutive testing position, reversing the direction of linear movement of the mobile test unit until the third signal indicator device becomes energized.

9. A method for conducting blow-down and differential pressure testing of the catalyst tubes of a tube and shell type catalytic reactor having an upper tube sheet and a multiplicity of reactor tubes each having the upper ends thereof extending downwardly from the upper tube sheet, comprising:

establishing a reactor tube identification system by which each of the multiplicity of reactor tube positions of the catalytic reactor is individually identified;

locating by tube identification sequence specific reactor tubes in a row of reactor tubes within the catalytic reactor;

selectively positioning a mobile test unit moveably on the upper tube sheet of the catalytic reactor, the mobile test unit having a test probe array including a plurality of linearly arranged test probes each having an air injection passage having a restricted orifice therein and each having a deformable resilient sealing member, said test probe array being moveable in unison relative to said mobile test unit between retracted positions with the sealing members located above the reactor tubes and testing positions with the deformable resilient sealing members located within respective reactor tube openings;

selectively expanding the deformable resilient sealing members and establishing sealing thereof within selected reactor tube openings;

establishing a blow-down flow path at least partially within at least one test probe bypassing the restricted orifice and communicating compressed air of said blow-down flow path with at least one reactor tube at a predetermined pressure and volume for reactor tube blow-down;

establishing a testing path within at least one test probe and through said restricted orifice and controllably injecting pressurized gas from said restricted orifice into reactor tubes at a predetermined test pressure and volume determined by air supply pressure and by orifice dimension for differential pressure testing of catalyst filled reactor tubes;

measuring the back-pressure existing at each of said test probes and developing an electronic signal representing the measured back-pressure; and electronically recording each of the back-pressure measurements in association with the reactor tube identification sequence thereof and providing a back-pressure measurement display.

10. The method of claim 9, comprising:
providing an alert indication in the electronic recording when any back-pressure measurement is out of a predetermined acceptable back-pressure range.

11. The method of claim 10, comprising:
said alert identification being displaying measured back-pressure within a designated pressure range in a first color displaying out of range high measured back-pressure in a second color and displaying out of range low measured back-pressure in a third color.

12. The method of claim 9, comprising:
locating a control unit away from the reactor tube openings of the upper tube sheet of the reactor, said control unit having a computer monitor, a computer driven printer and an on-board computer receiving processing and controlling display and printing of recorded back-pressure measurement data; and interconnecting said mobile test unit and said control unit with an umbilical providing electrical power, pneumatic supply and computer network connection between said mobile test unit and said control unit.

13. The method of claim 9, comprising:
providing signals on said mobile test unit confirming correlation of reactor tubes being engaged by said array of test probes and providing signals on said mobile test unit in the event the identification sequence of reactor tubes being engaged by said array of test probes differs from the identification sequence of the reactor tubes being engaged by said array of test probes.

14. The method of claim 9, comprising:
locating a control unit away from the reactor tube openings of the upper tube sheet of the reactor, said control unit having a color monitor, a computer driven color printer and an on-board computer receiving processing and controlling display and printing of recorded back-pressure data;

interconnecting the mobile test unit and the control unit with an umbilical providing electrical power, pneumatic supply and computer network connection; and providing at least one signal on said control unit confirming correlation of the identification of reactor tubes being engaged by said array of test probes and also providing signals on said control unit in the event the identification sequence of reactor tubes being engaged by said array of test probes differs from the identification sequence of the reactor tubes being engaged by said array of test probes.

15. A multi-tube differential pressure testing system for testing the differential pressure of catalyst filled tubes of tube and shell type catalytic reactors having an upper tube sheet defining a multiplicity of reactor tube openings and a multiplicity of catalyst filled reactor tubes having upper ends thereof fixed to the upper tube sheet at the reactor tube openings, comprising:

at least one mobile test unit adapted to be selectively positioned on the upper tube sheet of a catalytic reactor in pressure testing relation with a row of catalyst filled reactor tubes;

a test manifold being moveably mounted to said mobile test unit and having a plurality of test probes defining a test probe array, said test manifold being moveable to a test/blow-down position with said plurality of test probes engaging a selected plurality of reactor tubes and a non-test/blow-down position with said plurality of test probes retracted from the reactor tubes, said mobile test unit defining a test flow path for each test probe having a restricted orifice and defining a blow-down flow path for each test probe by-passing said restricted orifice, each of said blow-down flow paths having a blow-down valve selectively controlling the flow of compressed air through said blow-down flow path, said at least one mobile test unit measuring the pneumatic back-pressure of each test flow path and generating electronic signals being representative of the measured back-pressure of each test flow path;

a control unit being positionable in spaced relation with said at least one mobile test unit and having an on-board computer, computer monitor and computer driven printer for recording and displaying the electronic back-pressure measurements of individual test probes in correlation with the identification sequence of each reactor tube and printing the results of differential pressure testing of each reactor tube; and at least one umbilical interconnecting said at least one mobile test unit and said control unit and establishing an electrical power supply, pneumatic supply and computer network connection between said at least one mobile test unit and said control unit.

16. The multi-tube differential pressure testing system of claim 15, comprising:

a test probe actuator being mounted to said at least one mobile test unit and having a test probe mount supporting and moving said test probe array; and said plurality of test probes each being adjustable relative to said test probe mount and being independently positioned in correlation with the spacing of the reactor tubes being tested and being selectively vertically moveable between said test position and said non-test position relative to said test probe actuator when disabled reactor tube positions are encountered.

17. The multi-tube differential pressure testing system of claim 15, comprising:
said plurality of test probes each being selectively moveable to a non-test position relative to said test probe actuator when disabled reactor tube positions are encountered;
said test probes having sensors providing signals indicating said test and non-test positions; and
said on-board computer of said control unit receiving said test and non-test position signals and providing an electronic record of non-test for any disabled reactor tube position.

18. The multi-tube differential pressure testing system of claim 15, comprising:
at least one motor selectively moving said test probe actuator to a test position with lower portions of said test probes located within a selected plurality of reactor tubes to be tested and to a non-test position with said test probes retracted to positions above the selected plurality of reactor tubes.

19. The multi-tube differential pressure testing system of claim 15, comprising:
said test manifold being mounted for selective lateral movement relative to said at least one mobile test unit from a normal position to a laterally extended position to position said test probe array in testing registry with otherwise inaccessible reactor tubes.

20. The multi-tube differential pressure testing system of claim 15, comprising:
each of said test probes having a resilient seal member having a contracted condition permitting insertion thereof into and extraction thereof from a reactor tube and having an expanded condition developing a seal within a reactor tube; and
a seal actuator having force applying relation with said resilient seal member and being selectively actuated to cause change of said resilient seal from said contracted condition to said expanded condition and to permit said resilient seal to return from said expanded condition to said contracted condition.

21. The multi-tube differential pressure testing system of claim 20, comprising:
said seal actuator providing support for said resilient seal member and having a mechanical linkage being actuated for applying compression to said resilient seal member for change thereof to said expanded condition; and
said resilient seal member having a spring characteristic and being spring loaded during compression thereof and with the spring load thereof returning said resilient seal member to said contracted condition upon release of said compression.

22. The multi-tube differential pressure testing system of claim 21, comprising:
said mechanical linkage being a manually actuated toggle linkage having an actuating lever to which manual force is applied for actuation thereof; and
said toggle linkage having a locking position retaining said resilient seal member at said expanded condition.

23. The multi-tube differential pressure testing system of claim 15, comprising:
electronic test probe position indicator circuits being provided by said mobile test unit and having a an electronic contact member located adjacent each of said test probes; and
a contact actuator being supported by each of said test probes and actuating said electronic contact member to a test position when said test probes of said test manifold are located at test positions, said contact actuator positioning of said electronic contact member at a non-test position when its test probe is moved to a non-test position with respect to said test manifold, said electronic test probe position indicator circuit providing network signals representative of said test and non-test positions of said electronic contact member.

24. The multi-tube differential pressure testing system of claim 15, comprising:
a test wand support being provided on said mobile test unit;
a manually positioned and actuated test wand being removably supported by said test wand support near said test manifold and defining a wand test probe having a resilient seal member having a contracted condition permitting insertion thereof into and extraction thereof from a reactor tube and having an expanded condition developing a seal within a reactor tube;
a seal actuator being mounted to said manually positioned and actuated test wand and providing support for said resilient seal member, said seal actuator selectively applying compression to said resilient seal member for change thereof from said contracted condition to said expanded condition; and
flexible pneumatic tubes pneumatically connecting said wand test probe to said mobile test unit and being of sufficient length for manual movement of said test wand to a selected reactor tube and for conducting blow-down and differential pressure testing thereof.

25. The multi-tube differential pressure testing system of claim 24, comprising:
said seal actuator being a manually actuated toggle linkage having an actuating lever to which manual force is applied for actuation thereof; and
said manually actuated toggle linkage having a locking position retaining said resilient seal member at said expanded condition thereof.

26. The multi-tube differential pressure testing system of claim 24, comprising:
electronic test wand test completion and reset status circuits interfacing said mobile test unit and said test wand and each having an electrical contact being selectively actuated to provide a reactor tube test completion signal and to provide a reset signal; and
a contact actuator being supported by said test wand and selectively actuating said electrical contacts of said test completion and reset status circuits to provide wand status network signals for processing and recording by said computer of said control unit.

27. The multi-tube differential pressure testing system of claim 15, comprising:
a plurality of wheel assemblies being mounted to said at least one mobile test unit and establishing linear movement of said mobile test unit on the upper tube sheet of the reactor and coordinating movement of said at least one mobile test unit in substantially parallel relation with predetermined rows of reactor tubes;

at least one position signal indicator circuit being provided by said at least one mobile test unit and indicating incremental linear movement of at least one mobile test unit on the upper tube sheet of the reactor in correlation with reactor tube spacing; and a linear encoder being provided on at least one of said wheel assemblies and having a signal conductor being connected with said position signal indicator circuit, said linear encoder measuring linear movement of said at least one mobile test unit and providing position signals visible to operating personnel of said at least one mobile test unit and assisting operating personnel in precise location of said at least one mobile test unit relative to selected groups of reactor tubes.

28. The multi-tube differential pressure testing system of claim 15, comprising:

an actuator support being movably supported by said mobile test unit structure, said plurality of testing probes being mounted to said actuator support and being selectively positioned by movement of said actuator support in test and non-test positions relative to said mobile test unit structure;

at least one gas pressure operated actuator motor being supported by said mobile test unit structure and being selectively operated for moving said actuator support to said test position and to said non-test position; and an actuator gas supply being in controlling communication with said gas pressure operated actuator motor and having an actuator motor control valve being selectively actuatable to open and closed positions thereof and controlling supply of pressurized air to said at least one gas pressure operated actuator motor.

29. A multi-tube differential pressure testing system for differential pressure testing catalyst filled tubes of tube and shell type catalytic reactors having an upper tube sheet and multiple catalyst tubes arranged in multiple rows and having upper ends thereof fixed to the upper tube sheet and defining reactor tube openings, comprising:

at least one mobile test unit being selectively positioned in moveable relation on the upper tube sheet of a catalytic reactor in pressure testing relation with a plurality of reactor tube openings;

a plurality of test probes being moveably mounted to said mobile test unit and being simultaneously moveable relative to said at least one mobile test unit to a blow-down/test position in sealed gas pressure communicating engagement with a plurality of reactor tube openings and a non-test position with said plurality of test probes retracted from said reactor tube openings;

a blow-down and pressure testing gas delivery system being interconnected with said plurality of test probes and communicating pressurized gas to said plurality of test probes;

a differential pressure monitoring system measuring the back-pressure resulting from application of gas pressure at a selected test pressure into each of a plurality of reactor tube openings and having a differential pressure indicator system providing indication of the resulting differential pressure of each reactor tube being tested and providing electronic signals representative of the detected back-pressure of each reactor tube; and a computer system receiving the electronic signals representing the measured back-pressure of each of said plurality of reactor tubes and providing a computer generated record thereof.

30. The multi-tube differential pressure testing system of claim 29, comprising:

said at least one mobile test unit defining a plurality of test flow paths each being in communication with a respective one of said plurality of test probes and a plurality of blow-down flow paths each being in communication with a respective one of said plurality of test probes, each test flow path having a restricted orifice and each blow-down flow path bypassing said restricted orifice; and a plurality of blow-down valves each being disposed in compressed air controlling relation with a respective blow-down flow path and being opened to permit unrestricted flow of compressed air to a selected reactor tube via the respective blow-down flow path.

31. The multi-tube differential pressure testing system of claim 29, comprising:

a system specifically identifying each of the multiplicity of reactor tubes of the catalytic reactor tubes and enabling manual or automated location thereof; and said computer system assigning an identity to each of said multiplicity of reactor tubes of the catalytic reactor and providing said identity in said computer generated record and enabling workers to identify and service specific reactor tubes of the catalytic reactor via utilization of said computer generated record.

32. The multi-tube differential pressure testing system of claim 29, comprising:

a control unit being selectively positioned relative to the upper tube sheet of the catalytic reactor;

said at least one testing cart being a plurality of mobile test units; and umbilical elements, including electrical, pneumatic and computer network conductors interconnecting said control unit with said plurality of mobile test units.

33. The multi-tube differential pressure testing system of claim 29, comprising:

said computer system being located in said control unit and being connected by said umbilical elements for electronic communication with electronic signal systems of each of said mobile test units; and said computer system having a computer processor, keyboard data signal device, data printer and data memory system for processing and recording differential pressure signals resulting from testing each of said multiplicity of reactor tubes, printing a record identifying the test data of each reactor tube.

34. The multi-tube differential pressure testing system of claim 29, comprising:

an actuator support being movably supported by said testing cart structure, said plurality of test probes being mounted to said actuator support and being simultaneously moved by said actuator support;

a pressurized gas operated actuator selectively moving said actuator support and said plurality of test probes upwardly to said non-test position and downwardly to said test position; and an actuator gas supply being in controlling communication with said gas operated actuator and having an actuator control valve being selectively actuatable for simultaneous movement of said actuator support and said plurality of test probes to said non-test position and said testing position.

35. The multi-tube differential pressure testing system of claim 29, comprising:

a plurality of wheel assemblies being mounted to said at least one mobile test unit and establishing linear movement of said mobile test unit on the upper tube sheet of the reactor and coordinating movement of said at least one mobile test unit in substantially parallel relation with predetermined rows of reactor tubes;

at least one position signal indicator circuit being provided by said at least one mobile test unit and indicating incremental linear movement of at least one mobile test unit on the upper tube sheet of the reactor in correlation with reactor tube spacing; and a linear encoder being provided on at least one of said wheel assemblies and having a signal conductor being connected with said position signal indicator circuit, said linear encoder measuring linear movement of said at least one mobile test unit and providing position signals visible to operating personnel of said at least one mobile test unit and assisting operating personnel in precise location of said at least one mobile test unit relative to selected groups of reactor tubes.

36. The multi-tube differential pressure testing system of claim 29, comprising:

a test probe actuator being mounted to said at least one mobile test unit and having a test probe mount supporting and moving said test probe array; and said plurality of test probes each being adjustable relative to said test probe mount and being independently positioned in correlation with the spacing of the reactor tubes being tested and being selectively vertically moveable between said test position and said non-test position relative to said test probe actuator when disabled reactor tube positions are encountered.

37. The multi-tube differential pressure testing system of claim 29, comprising:

said plurality of test probes each being selectively moveable to a non-test position relative to said test probe actuator when disabled reactor tube positions are encountered;

said test probes having sensors providing signals indicating said test and non-test positions; and said on-board computer of said control unit receiving said test and non-test position signals and providing an electronic record of non-test for any disabled reactor tube position.

38. The multi-tube differential pressure testing system of claim 29, comprising:

at least one motor selectively moving said test probe actuator to a test position with lower portions of said test probes located within a selected plurality of reactor tubes to be tested and to a non-test position with said test probes retracted to positions above the selected plurality of reactor tubes.

39. The multi-tube differential pressure testing system of claim 29, comprising:

said test manifold being mounted for selective lateral movement relative to said at least one mobile test unit from a normal position to a laterally extended position to position said test probe array in testing registry with otherwise inaccessible reactor tubes.

40. The multi-tube differential pressure testing system of claim 29, comprising:

each of said test probes having a resilient seal member having a contracted condition permitting insertion thereof into and extraction thereof from a reactor tube and having an expanded condition developing a seal within a reactor tube; and a seal actuator having force applying relation with said resilient seal member and being selectively actuated to cause change of said resilient seal from said contracted condition to said expanded condition and to permit said resilient seal to return from said expanded condition to said contracted condition.

41. The multi-tube differential pressure testing system of claim 40, comprising:

said seal actuator providing support for said resilient seal member and having a mechanical linkage being actuated for applying compression to said resilient seal member for change thereof to said expanded condition; and said resilient seal member having a spring characteristic and being spring loaded during compression thereof and with the spring load thereof returning said resilient seal member to said contracted condition upon release of said compression.

42. The multi-tube differential pressure testing system of claim 41, comprising:

said mechanical linkage being a manually actuated toggle linkage having an actuating lever to which manual force is applied for actuation thereof; and said toggle linkage having a locking position retaining said resilient seal member at said expanded condition.

43. The multi-tube differential pressure testing system of claim 29, comprising:

electronic test probe position indicator circuits being provided by said mobile test unit and having a an electronic contact member located adjacent each of said test probes; and a contact actuator being supported by each of said test probes and actuating said electronic contact member to a test position when said test probes of said test manifold are located at test positions, said contact actuator positioning of said electronic contact member at a non-test position when its test probe is moved to a non-test position with respect to said test manifold, said electronic test probe position indicator circuit providing network signals representative of said test and non-test positions of said electronic contact member.

44. The multi-tube differential pressure testing system of claim 29, comprising:

a test wand support being provided on said mobile test unit;

a manually positioned and actuated test wand being removably supported by said test wand support near said test manifold and defining a wand test probe having a resilient seal member having a contracted condition permitting insertion thereof into and extraction thereof from a reactor tube and having an expanded condition developing a seal within a reactor tube;

a seal actuator being mounted to said manually positioned and actuated test wand and providing support for said resilient seal member, said seal actuator selectively applying compression to said resilient seal member for change thereof from said contracted condition to said expanded condition; and flexible pneumatic tubes pneumatically connecting said wand test probe to said mobile test unit and being of sufficient length for manual movement of said test wand to a selected reactor tube and for conducting blow-down and differential pressure testing thereof.

45. The multi-tube differential pressure testing system of claim 44, comprising:

said seal actuator being a manually actuated toggle linkage having an actuating lever to which manual force is applied for actuation thereof; and said manually actuated toggle linkage having a locking position retaining said resilient seal member at said expanded condition thereof.

46. The multi-tube differential pressure testing system of claim 44, comprising:

electronic test wand test completion and reset status circuits interfacing said mobile test unit and said test wand and each having an electrical contact being selectively actuated to provide a reactor tube test completion signal and to provide a reset signal; and a contact actuator being supported by said test wand and selectively actuating said electrical contacts of said test completion and reset status circuits to provide wand status network signals for processing and recording by said computer of said control unit.

47. The multi-tube differential pressure testing system of claim 29, comprising:

a plurality of wheel assemblies being mounted to said at least one mobile test unit and establishing linear movement of said mobile test unit on the upper tube sheet of the reactor and coordinating movement of said at least one mobile test unit in substantially parallel relation with predetermined rows of reactor tubes;

at least one position signal indicator circuit being provided by said at least one mobile test unit and indicating incremental linear movement of at least one mobile test unit on the upper tube sheet of the reactor in correlation with reactor tube spacing; and a linear encoder being provided on at least one of said wheel assemblies and having a signal conductor being connected with said position signal indicator circuit, said linear encoder measuring linear movement of said at least one mobile test unit and providing position signals visible to operating personnel of said at least one mobile test unit and assisting operating personnel in precise location of said at least one mobile test unit relative to selected groups of reactor tubes.

48. The multi-tube differential pressure testing system of claim 29, comprising:

an actuator support being movably supported by said mobile test unit structure, said plurality of testing probes being mounted to said actuator support and being selectively positioned by movement of said actuator support in test and non-test positions relative to said mobile test unit structure;

at least one gas pressure operated actuator motor being supported by said mobile test unit structure and being selectively operated for moving said actuator support to said test position and to said non-test position; and an actuator gas supply being in controlling communication with said gas pressure operated actuator motor and having an actuator motor control valve being selectively actuatable to open and closed positions thereof and controlling supply of pressurized air to said at least one gas pressure operated actuator motor.

* * * * *